US008101622B2

(12) United States Patent
Baik et al.

(10) Patent No.: US 8,101,622 B2
(45) Date of Patent: Jan. 24, 2012

(54) PYRIDOPYRIMIDINONE INHIBITORS OF PI3Kα AND MTOR

(75) Inventors: Tae-Gon Baik, Foster CIty, CA (US);
Sunghoon Ma, Foster City, CA (US);
Chris A. Buhr, Redwood City, CA (US);
John M. Nuss, Danville, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 12/569,760

(22) Filed: Sep. 29, 2009

(65) Prior Publication Data

US 2010/0087456 A1  Apr. 8, 2010

Related U.S. Application Data

(60) Provisional application No. 61/194,761, filed on Sep. 30, 2008.

(51) Int. Cl.
*C07D 471/04* (2006.01)
*A61K 31/519* (2006.01)
*A61P 35/00* (2006.01)

(52) U.S. Cl. .................. 514/264.11; 544/279
(58) Field of Classification Search .................. 544/279; 614/264.11
See application file for complete search history.

(56) References Cited

U.S. PATENT DOCUMENTS

| 7,696,213 | B2* | 4/2010 | Cheng et al. | ............. 514/264.11 |
| 2003/0100572 | A1* | 5/2003 | Metcalf et al. | ............. 514/264.11 |
| 2004/0009993 | A1 | 1/2004 | Angiolini et al. | |
| 2005/0182078 | A1 | 8/2005 | Barvian et al. | |
| 2009/0270430 | A1* | 10/2009 | Baik et al. | ................. 514/264.11 |
| 2010/0209340 | A1* | 8/2010 | Buhr et al. | ................... 424/1.11 |

FOREIGN PATENT DOCUMENTS

| EP | 1 277 738 A1 | 1/2003 |
| EP | 1 364 950 A1 | 11/2003 |
| JP | 2004-083587 | 3/2004 |
| WO | WO 96/34867 | 11/1996 |
| WO | WO 98/33798 | 8/1998 |
| WO | WO 01/55148 A1 | 8/2001 |
| WO | WO 01/70741 A1 | 9/2001 |
| WO | WO 03/088972 A1 | 10/2003 |
| WO | WO 03/093290 A2 | 11/2003 |
| WO | WO 2004/063195 A1 | 7/2004 |
| WO | WO 2004/089930 A1 | 10/2004 |
| WO | WO 2005/040337 A2 | 5/2005 |
| WO | WO 2005/082903 A1 | 9/2005 |
| WO | WO 2005/105801 A1 | 11/2005 |
| WO | WO 2006/065703 A1 | 6/2006 |

OTHER PUBLICATIONS

Angiolini, M., et al., "Solid-phase synthesis of pyrido[2,3-d]pyrimidin-7-ones," Tetrahedron Letters, (2005), vol. 46, pp. 8749-8752.

Barvian, M., et al., "Pyrido[2,3-d]pyrimidin-7-one inhibitors of cyclin-dependent kinases," J. Med. Chem., (2000) vol. 43, pp. 4606-4616.
Boschelli, D.H., et al., "Synthesis and tyrosine kinase inhibitory activity of a series of 2-amino-8H-pyrido[2,3-d]pyrimidines: identification of potent, selective platelet-derived growth factor receptor tyrosine kinase inhibitors," J. Med. Chem., (1998) vol. 41, pp. 4365-4377.
Hamby, J.M., et al., "Structure-activity relationships for a novel series of pyrido[2,3-d]pyrimidine tyrosine kinase inhibitors," J. Med. Chem., (1997) vol. 40, pp. 2296-2303.
Klutchko, S.R., et al., "2-Substituted aminopyrido[2,3-d]pyrimidin-7(8H)-ones. Structure-activity relationships against selected tyrosine kinases and in vitro and in vivo anticancer activity," J. Med Chem. (1998), vol. 41 pp. 3276-3292.
Toogood. P.L. et al., "Discovery of a potent and selective inhibitor of cyclin-dependent kinase 4/6," J. Med. Chem., (2005) vol. 48, pp. 2388-2406.
Trumpp-Kallmeyer, 5., et al., "Development of a binding model to protein tyrosine kinases for substituted pyrido[2,3-d]pyrimidine inhibitors," J. Med. Chem., (1998) vol. 41,pp. 1752-1763.
Database Registry, CAS registration No. 400881-06-3, (date of publication Mar. 14, 2002), Chemical Abstracts Service, STN North America, Columbus, Ohio, www.cas.org/stn.html.
Database Registry, CAS registration No. 400878-58-2, (date of publication Mar. 14, 2002), Chemical Abstracts Service, STN North America, Columbus, Ohio, www.cas.org/stn.html.
Database Registry, CAS registration No. 374910-33-5 (date of publication Dec. 13, 2001), Chemical Abstracts Service, STN North America, Columbus, Ohio, www.cas.org/stn.html. Database Registry, CAS registration No. 294874-94-5 (date of publication Oct. 12, 2000), Chemical Abstracts Service, STN North America, Columbus, Ohio, www.cas.org/stn.html.
Database Registry, CAS registration No. 405295-77-4 (date of publication Apr. 12, 2002), Chemical Abstracts Service, STN North America, Columbus, Ohio, www.cas.org/stn.html.
International Search Report dated Aug. 19, 2008.

* cited by examiner

*Primary Examiner* — James O Wilson
*Assistant Examiner* — Cecilia M Jaisle
(74) *Attorney, Agent, or Firm* — Honigman Miller Schwartz & Cohn, LLP; Heidi M. Berven; Jonathan O'Brien

(57) ABSTRACT

The invention is directed to Compounds of Formula I:

optionally as a single stereoisomer or mixture of stereoisomers thereof, and additionally optionally as a pharmaceutically acceptable salt thereof; as well as methods of making and using the compounds.

16 Claims, No Drawings

PYRIDOPYRIMIDINONE INHIBITORS OF PI3Kα AND MTOR

This application is a nonprovisional application which claims priority to U.S. Provisional Patent Application Ser. No. 61/194,761 filed on Sep. 30, 2008, now expired, the disclosures of which are incorporated herein by reference.

BACKGROUND OF THE INVENTION

1. Field of the Invention

This invention relates to the field of protein kinases and inhibitors thereof. In particular, the invention relates to inhibitors of phosphatidylinositol 3-kinase (PI3K) signaling pathways, and methods of their use.

2. Summary of the Related Art

The PI3K pathway regulates cell growth, proliferation and survival, and is dysregulated with high frequency in human tumors. PI3K pathway activation in tumors occurs via multiple mechanisms including prevalent mutation and amplification of the PIK3CA gene (which encodes the p110 subunit of PI3Kα), or downregulation of the lipid phosphatase PTEN. Downstream of PI3K, mTOR controls cell growth and proliferation through its two distinct signaling complexes: mTORC1 and mTORC2. Given the role of PI3K signaling on critical cellular functions, an inhibitor that targets both PI3K and mTOR could provide therapeutic benefit to patient populations with tumors harboring activating mutations in PIK3CA or Ras, PTEN-deletion, or where tumors are upregulated in growth factor signaling.

Phosphatidylinositol 3-kinase (PI3Kα), a dual specificity protein kinase, is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation and differentiation processes. Increased copy number and expression of PIK3CA is associated with a number of malignancies such as ovarian cancer (Campbell et al., *Cancer Res* 2004, 64, 7678-7681; Levine et al., *Clin Cancer Res* 2005, 11, 2875-2878; Wang et al., *Hum Mutat* 2005, 25, 322; Lee et al., *Gynecol Oncol* 2005, 97, 26-34), cervical cancer, breast cancer (Bachman, et al. *Cancer Biol Ther* 2004, 3, 772-775; Levine, et al., supra; Li et al., *Breast Cancer Res Treat* 2006, 96, 91-95; Saal et al., *Cancer Res* 2005, 65, 2554-2559; Samuels and Velculescu, *Cell Cycle* 2004, 3, 1221-1224), colorectal cancer (Samuels, et al. *Science* 2004, 304, 554; Velho et al. *Eur J Cancer* 2005, 41, 1649-1654), endometrial cancer (Oda et al. *Cancer Res.* 2005, 65, 10669-10673), gastric carcinomas (Byun et al., *Int J Cancer* 2003, 104, 318-327; Li et al., supra; Velho et al., supra; Lee et al., *Oncogene* 2005, 24, 1477-1480), hepatocellular carcinoma (Lee et al., id.), small and non-small cell lung cancer (Tang et al., *Lung Cancer* 2006, 51, 181-191; Massion et al., *Am J Respir Crit Care Med* 2004, 170, 1088-1094), thyroid carcinoma (Wu et al., *J Clin Endocrinol Metab* 2005, 90, 4688-4693), acute myelogenous leukemia (AML) (Sujobert et al., *Blood* 1997, 106, 1063-1066), chronic myelogenous leukemia (CML) (Hickey and Cotter *J Biol Chem* 2006, 281, 2441-2450), and glioblastomas (Hartmann et al. *Acta Neuropathol (Berl)* 2005, 109, 639-642; Samuels et al., supra).

In view of the important role of PI3Kα in biological processes and disease states, inhibitors of this protein kinase are desirable.

The mammalian target of rapamycin, mTOR, is a protein kinase that integrates both extracellular and intracellular signals of cellular growth, proliferation, and survival. Extracellular mitogenic growth factor signaling from cell surface receptors and intracellular pathways that convey hypoxic stress, energy and nutrient status all converge at mTOR. mTOR exists in two distinct complexes: mTOR complex 1 (mTORC1) and mTOR complex 2 (mTORC2). mTORC1 is a key mediator of transcription and cell growth (via its substrates p70S6 kinase and 4E-BP1) and promotes cell survival via the serum and glucocorticoid-activated kinase SGK, whereas mTORC2 promotes activation of the pro-survival kinase AKT. Given its central role in cellular growth, proliferation and survival, it is perhaps not surprising that mTOR signaling is frequently dysregulated in cancer and other diseases (Bjornsti and Houghton *Rev Cancer* 2004, 4(5), 335-48; Houghton and Huang *Microbiol Immunol* 2004, 279, 339-59; Inoki, Corradetti et al. *Nat Genet* 2005, 37(1), 19-24).

mTOR is a member of the PIKK (PI3K-related Kinase) family of atypical kinases which includes ATM, ATR, and DNAPK, and its catalytic domain is homologous to that of PI3K. Dysregulation of PI3K signaling is a common function of tumor cells. In general, mTOR inhibition may be considered as a strategy in many of the tumor types in which PI3K signaling is implicated such as those discussed below.

In treating breast cancer, inhibition of PI3K signaling is critical for the activity of EGFR family inhibitors such as the anti-HER2 antibody trastuzumab (Nagata, Lan et al., *Cancer Cell* 2004, 6(2), 117-27), and loss of PTEN correlates with trastuzumab resistance (Pandolfi *N Engl J Med* 2004, 351 (22), 2337-8; Nahta, Yu et al. *Nat Clin Pract Oncol* 2006, 3(5), 269-280). Therefore, inhibitors of PI3K signaling may be particularly useful in HER2 positive tumors that either fail to respond or become resistant to trastuzumab.

Mantle cell lymphoma (MCL) is usually characterized by hyperactivation of cyclin D and subsequent cell cycle dysregulation. Transcription of cyclin D is largely mediated by mTOR signaling, and rapamycin, an allosteric inhibitor of mTOR kinase activity, has been reported to downregulate cyclin D levels in MCL cell lines in vitro (Dal Col, Zancai et al. *Blood* 2008, 111(10), 5142-51).

In renal cell carcinoma, mTOR-promoted translation of hypoxia-inducible transcription factor (HIF1α), and resulting enhancement of the expression of vascular growth factors, may be particularly relevant in the case of tumors bearing loss of function mutations in the von Hippel-Lindau (VHL) protein. This protein serves to block proteaseome-mediated destruction of HIF and thereby causes constitutive expression of proangiogenic growth factors (Thomas, Tran et al. *Nat Med* 2006, 12(1), 122-7). Such mutations are particularly prevalent in renal cell carcinoma, and may underlie the promising clinical activity seen with mTOR inhibitors in this disease (Atkins, Hidalgo et al. *J Clin Oncol* 2004, 22(5), 909-18; Motzer, Hudes et al. *J Clin Oncol* 2007, 25(25), 3958-64).

PI3K is activated in blasts from acute myelogenous leukemia (AML) patients and may contribute not only to the pathophysiology of the disease but also to chemotherapy resistance. AML cells consistently express the p110δ isoform, and inhibition of PI3Kδ reduces proliferation and survival of AML cells without affecting normal hematopoietic progenitors (Sujobert, Bardet et al. *Blood* 2005, 106(3), 1063-6; Billottet, Grandage et al. *Oncogene* 2006, 25(50), 6648-

6659). On the other hand, PI3K pathway activation has been associated with improved overall and relapse-free survival in newly diagnosed AML patients (Tamburini, Elie et al. *Blood* 2007, 110(3), 1025-8).

In chronic myelogenous leukemia (CML), the BCR-ABL oncogene signals through the p85 subunit of PI3K, mediating leukemogenesis, cell growth and cell survival (Skorski, Bellacosa et al. *Embo J* 1997, 16(20), 6151-61). A similar mechanism may be involved in growth and survival of NPM/ALK-transformed anaplastic large cell lymphoma cells (Bai, Ouyang et al. *Blood* 2000, 96(13), 4319-27). In addition, the p110γ subunit may be transcriptionally upregulated by BCR-ABL, and as such PI3Kγ, which is preferentially expressed in hematopoietic cells, may be an important target in drug-resistant CML (Hickey and Cotter *Biol Chem* 2006, 281(5), 2441-50).

The PI3K pathway was also found to be activated in diffuse large B cell lymphoma (DLBCL) cell lines and tumor samples, and PI3K inhibition led to apoptosis in several DLBCL cell lines (Uddin, Hussain et al. *Blood* 2006, 108 (13), 4178-86).

Activation of the IGF1R receptor and downstream PI3K-mTOR pathway signaling is implicated in the genesis and progression of several subtypes of sarcoma (Hernando, Charytonowicz et al. *Nat Med* 2007, 13(6), 748-53; Wan and Helman *Oncologist* 2007, 12(8), 1007-18).

Rhabdomyosarcoma, one of the most common childhood sarcomas, is reported to be addicted to insulin-like growth factor I receptor signaling as measured by elevated AKT signaling (Cao, Yu et al. *Cancer Res* 2008, 68(19), 8039-8048). Insulin-like growth factor II is over-expressed in these cancers and the anti-tumor effect of rapamycin, an mTORC1 inhibitor, has been evaluated and reported to inhibit rhabdomyosarcoma xenograft growth (Wan, Shen et al. *Neoplasia* 2006, 8(5), 394-401).

Amplification of PIK3CA in ovarian cancer was one of the first indications that PI3Kα functions as a human oncogene (Shayesteh, Lu et al. *Nat Genet,* 1999, 21(1), 99-102). Both PI3K amplification and loss of PTEN have been associated with resistance to cisplatin in ovarian tumors (Lee, Choi et al. *Gynecol Oncol* 2005, 97(1) 26-34).

Both PTEN loss and PI3K mutation or amplification are common in endometrial tumors, with PTEN mutations found in up to 80% of the endometrioid subtype of endometrial carcinomas (Obata, Morland et al. *Cancer Res* 1998, 58(10), 2095-7). mTOR activation is quite common in endometrial tumors, promoted by downregulation of the LKB1 and/or TSC2 tumor suppressors, and dual inhibition of both the PI3K and mTOR axes may be a particularly useful strategy (Lu, Wu et al. *Clin Cancer Res* 2008, 14(9), 2543-50).

PI3K signaling may play an important role in many lung tumors; a recent study found overexpression of AKT and loss of PTEN in 41% and 46% of non small cell lung carcinoma (NSCLC) samples respectively (Tang, He et al. *Lung Cancer* 2006, 51(2), 181-91). Another recent analysis found 74% of NSCLC tumors with reduced or absent PTEN expression (Marsit, Zheng et al. *Hum Pathol* 2005, 36(7), 768-76). Frequent amplification of PIK3CA has also been demonstrated in various subtypes of lung cancer, including small cell (67%), squamous (70%), large cell (38%) and adenocarcinoma (19%) (Massion, Taflan et al. *Am J Respir Crit Care Med* 2004, 170(10), 1088-94). Notably, resistance to the EGFR inhibitor gefitinib correlates with failure to downregulate AKT signaling and loss of PTEN (Kokubo, Gemma et al. *Br J Cancer* 2005, 92(9), 1711-9), and KRAS status may also play an important role in determining response to EGFR inhibitors (Pao, Wang et al. *Pub Library of Science Med* 2005, 2(1), e17).

PI3K is mutated in 13-32% of colorectal tumors (Velho, Oliveira et al. *Eur J Cancer* 2005, 41(11), 1649-54; Foukas, Claret et al. *Nature,* 2006, 441(7091), 366-370), and loss of PTEN is observed in a high proportion of colorectal tumors, particularly those that display microsatellite instability (Goel, Arnold et al. *Cancer Res* 2004, 64(9), 3014-21; Nassif, Lobo et al. *Oncogene* 2004, 23(2), 617-28). Additionally, KRAS (which can also lead to upregulation of PI3K signaling) is the most frequently mutated oncogene in colorectal tumors (Bos *Cancer Res* 1989. 49(17), 4682-9; Fearon *Ann N Y Acad Sci* 1995, 768, 101-10). PI3K pathway dysregulation has also been implicated in impaired response to the anti-EGFR antibody cetuximab, and may also be of use in augmenting the response to chemotherapy (Perrone, Lampis et al. *Ann Oncol* 2009, 20(1), 84-90).

PTEN expression was found to be abnormally low in 36% of gastric carcinomas, and a similar proportion of tumors were found to have genomic amplifications of PIK3CA (Byun, Cho et al. *Int J Cancer* 2003, 104(3), 318-27).

PI3K activating mutations were reported to be found at high frequency in hepatocellular tumors (Lee, Soung et al. *Oncogene* 2005, 24(8), 1477-80). Furthermore, PTEN protein levels are decreased in up to 40% of liver tumors, and correlate inversely with pathological grade and disease progression (Hu, Huang et al. *Cancer* 2003, 97(8), 1929-40; Wan, Jiang et al. *Cancer Res Clin Oncol* 2003, 129(2), 100-6).

Loss of PTEN protein expression occurs in 18-19% of primary melanomas and 29-38% of melanoma cell lines, and is associated with increased tumor thickness (Guldberg, thor Straten et al. *Cancer Res* 1997, 57(17), 3660-3; Tsao, Zhang et al. *Cancer Res* 2000, 60(7), 1800-4; Whiteman, Zhou et al. *Int J Cancer* 2002, 99(1), 63-7; Goel, Lazar et al. *J Invest Dermatol* 126(1), 2006, 154-60).

Pancreatic tumors have a very high incidence of KRAS mutation, which elicits downstream activation of the PI3K pathway. In addition, decreased PTEN function has been reported in pancreatic cancer cell lines and tumor specimens, resulting in activated NFκB and stabilization of MYC (Asano, Yao et al. *Oncogene* 2004, 23(53), 8571-80).

Prostate carcinoma is characterized by frequent loss of PTEN function (Cairns, Okami et al. *Cancer Res* 1997, 57(22), 4997-5000; Gray, Stewart et al. *Br J Cancer* 1998, 78(10), 1296-300; Wang, Parsons et al. *Clin Cancer Res* 1998, 4(3), 811-5; Whang, Wu et al. *Proc Natl Acad Sci USA* 1998, 95(9), 5246-50), and PI3K inhibitors might have particular utility in this disease (Majumder and Sellers *Oncogene* 2005, 24(50) 7465-74). Recent data suggests that PTEN loss may play a fundamental role in expansion of a tumor stem cell-like population (Wang, Garcia et al. *Proc Natl Acad Sci USA* 2006, 103(5), 1480-5). There is extensive crosstalk between androgen receptor (AR) and PI3K pathway signaling, and PI3K/AKT or mTOR inhibition has shown promise in both androgen-dependent and independent preclinical models of prostate cancer (Lu, Ren et al. *Int J Oncol* 2006, 28(1), 245-51; Mulholland, Dedhar et al. *Oncogene* 25(3), 2006, 329-37; Xin, Teitell et al. *Proc Natl Acad Sci USA* 1 2006, 03(20), 7789-94; Mikhailova, Wang et al. *Adv Exp Med Biol* 2008, 617, 397-405; Wang, Mikhailova et al. *Oncogene* 2008, 27(56), 7106-7117).

PI3K is frequently mutated in thyroid carcinoma, particularly in the anaplastic subtype (Garcia-Rostan, Costa et al. *Cancer Res* 2005, 65(22), 10199-207). In a separate study, PI3K mutations were found to be relatively rare in thyroid arcinomas, but PI3K amplification was frequently found in follicular thyroid carcinoma (Wu, Mambo et al. *J Clin Endocrinol Metab* 2005, 90(8), 4688-93).

Anaplastic large cell lymphoma (ALCL) patients express an activated form of ALK kinase that results from a fusion of the nucleophosmin gene with the ALK kinase gene. The resulting fusion protine NPM-ALK is causally associated with ALCL and results in elevated mTOR signaling.

Hamaratomas, Angiomyelolipomas, TSC-Associated and Sporadic Lymphangioleiomyomatosis: Cowden's disease (multiple hamaratoma syndrome) is primarily the result of hereditary loss of function of PTEN. Patients develop hamaratomous neoplasms primarily of the skin and thyroid. Tuberous sclerosis patients develop benign hamaratomas in the lung, brain, kidneys, skin, and heart due to mutations in either TSC1 or TSC2. A large percentage of these patients also develop angiomyelolipomas (Bissler, McCormack et al. *N Engl J Med* 2008, 358(2), 140-151). Many female TSC patients also develop a progressive lung disease, lymphangioleiomyomatosis, which is a result of smooth muscle cell infiltration into the lungs (Bissler, et al. id.). While these tumors are benign, severe complications may arise as a consequence of the growth of these tumors and infiltrates.

Recent studies found that patients with sclerosing hemangioma, a rare lung tumor, have 84% reduced expression of STK11/LKB1 and elevated mTOR phosphorylation and signaling (Randa M. S. Amin *Pathology International* 2008, 58(1), 38-44). Germline mutations in LKB1/STK1 is the causal underlying mutation in Peutz-Jeghers syndrome (PJS), an autosomal dominant disorder.

The primary form of treatment for head and neck cancer is surgery and/or radiation. There is evidence that radioresistance may occur via upregualtion of the PI3K/mTOR pathway (Gupta, McKenna et al. *Clin Cancer Res* 2002, 8(3), 885-892). Measurement of reduced AKT phosphorylation in patients correlated with better local control of the cancer.

In addition to the above tumor types, mTOR is particularly implicated in other diseases. For example, rapamycin is in clinical study for therapeutic treatment of neurofibromatosis. Mutation of the neurofibromatosis-1 gene in neurofibromatosis results in activation of the mTOR pathway (Ferner *Eur J Hum Genet* 2006, 15(2), 131-138; Sabatini *Nat Rev Cancer* 2006, 6(9), 729-734; Johannessen, Johnson et al. *Current Biology* 2008, 18(1), 56-62). In addition, rapamycin is in clinical study for macular degeneration, macular edema, and myeloid leukemia. Rapamycin is also being studied clinically in patients with systemic lupus and autoimmune lymphoproliferative syndrome (ALPS).

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The invention provides compounds that inhibit, regulate, and/or modulate PI3K and mTOR that are useful in the treatment of hyperproliferative diseases, such as cancer, in humans. This invention also provides methods of making the compound, methods of using such compounds in the treatment of hyperproliferative diseases in humans and to pharmaceutical compositions containing such compounds.

A first aspect of the invention provides a compound of Formula I

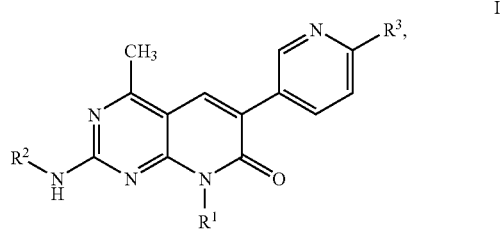

optionally as a single stereoisomer or mixture of stereoisomers thereof, and additionally optionally as a pharmaceutically acceptable salt thereof, wherein $R^1$ is tetrahydrofuranyl or tetrahydropyranyl;

$R^2$ is hydrogen or alkyl;

$R^3$ is $-NR^4R^{4a}$; and $R^4$ and $R^{4a}$ are independently selected from hydrogen and alkyl.

In a second aspect, the invention is directed to a pharmaceutical composition which comprises a compound of Formula I optionally as a single stereoisomer or mixture of stereoisomers thereof, and additionally optionally as a pharmaceutically acceptable salt thereof, and a pharmaceutically acceptable carrier, excipient, or diluent.

In a third aspect, the Invention provides a method for treating a disease, disorder, or syndrome which method comprises administering to a patient a therapeutically effective amount of a compound of Formula I optionally as a single stereoisomer or mixture of stereoisomers thereof, and additionally optionally as a pharmaceutically acceptable salt thereof, or a pharmaceutical composition comprising a therapeutically effective amount of a compound of Formula I optionally as a single stereoisomer or mixture of stereoisomers thereof, and additionally optionally as a pharmaceutically acceptable salt thereof, and a pharmaceutically acceptable carrier, excipient, or diluent.

In a fourth aspect, the Invention provides a method for preparing a Compound of Formula I, comprising:

(a) reacting an intermediate of formula 9:

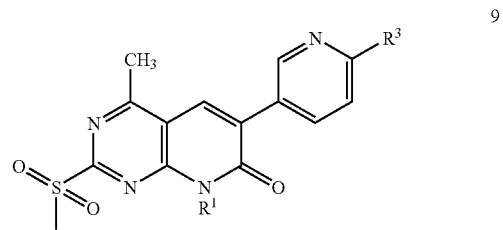

where $R^1$ and $R^3$ are as defined in the Summary of the Invention for a Compound of Formula I; with an intermediate of formula $R^2NH_2$ where $R^2$ is as defined in the Summary of the Invention for a Compound of Formula I, to yield a Compound of Formula I; or (b) reacting an intermediate of formula 7:

where $R^1$ is as defined in the Summary of the Invention for a Compound of Formula I; with an intermediate of formula 8

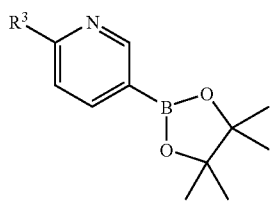

where $R^3$ is as defined in the Summary of the Invention, to yield a Compound of Formula I(f):

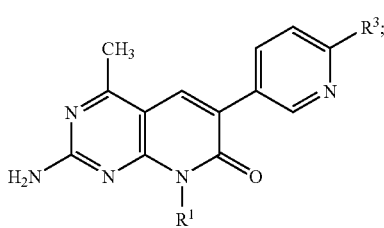

and (c) optionally alkylating $R^3$ when $R^3$ is —$NH_2$ or —$NHR^{4a}$ and $R^{4a}$ is alkyl; and (d) optionally further resolving individual isomers.

DETAILED DESCRIPTION OF THE INVENTION

Abbreviations and Definitions

The following abbreviations and terms have the indicated meanings throughout:

| Abbreviation | Meaning |
|---|---|
| ° C. | degrees Celsius |
| d | doublet |
| dd | doublet of doublet |
| dt | doublet of triplet |
| DBU | diaza(1,3)bicyclo[5.4.0]undecane |
| DCM | dichloromethane |
| DMF | N,N-dimethylformamide |
| DMSO | dimethyl sulfoxide |
| DTT | dithiothreitol |
| EI | electron impact ionization |
| equiv | equivalent(s) |
| EtOH | ethanol |
| g | gram(s) |
| h or hr | hour(s) |
| HPLC | high pressure liquid chromatography |
| L | liter(s) |
| LC/MS | liquid chromatography/mass spectral analysis |
| m | multiplet |
| MeOH | methanol |
| mg | milligram(s) |
| MHz | megahertz (frequency) |
| min | minute(s) |
| mL | milliliter(s) |
| μL | microliter(s) |
| mmol | millimole(s) |
| mol | mole(s) |
| N | normal or normality |
| nM | nanomolar |
| NMR | nuclear magnetic resonance spectroscopy |
| q | quartet |
| RT or rt | room temperature |
| s | singlet |
| t or tr | triplet |

The symbol "—" means a single bond, "═" means a double bond, "≡" means a triple bond, "----"means a single or double bond. The symbol "⤳"refers to a group on a double-bond as occupying either position on the terminus of a double bond to which the symbol is attached; that is, the geometry, E- or Z-, of the double bond is ambiguous. When a group is depicted removed from its parent formula, the "⤳"symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It is understood by one of ordinary skill in the art that the aforementioned descriptive techniques are common in the chemical arts to provide brevity and simplicity to description of otherwise complex structures.

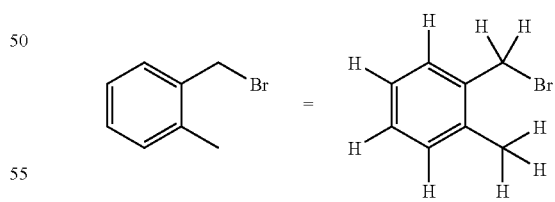

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkyl" means a linear saturated monovalent hydrocarbon radical of one to six carbon atoms or a branched saturated monovalent hydrocarbon radical of three to 6 carbon atoms, e.g., methyl, ethyl, propyl, 2-propyl, butyl (including all isomeric forms), or pentyl (including all isomeric forms), and the like.

"Amino" means —$NH_2$.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Stereosiomer" means any of two or more isomers containing the same atoms bonded to each other in an identical manner but differing from each other in the spatial arrangement of the atoms or groups of atoms. "Stereoisomer" includes, for example, an enantiomer, a geometric isomer, a diastereomer, a rotamer, cis-isomer, trans-isomer, and conformational isomer.

"Tetrahydrofuranyl" includes tetrahydrofuran-2-yl and tetrahydrofuran-3-yl and any stereoisomer and mixture of stereoisomers thereof.

"Tetrahydropyranyl" includes tetrahydropyran-2-yl, tetrahydropyran-3-yl, and tetrahydropyran-4-yl and any stereoisomer and mixture of stereoisomers thereof.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

"Yield" for each of the reactions described herein is expressed as a percentage of the theoretical yield.

EMBODIMENTS OF THE INVENTION

The following paragraphs present a number of embodiments of compounds of the invention. In each instance the embodiment includes both the recited compounds, as well as a single stereoisomer or mixture of stereoisomers thereof, as well as a pharmaceutically acceptable salt thereof.

Another embodiment of the Invention is directed to a Compound of Formula I wherein $R^2$ is hydrogen; and all other groups are as defined in the Summary of the Invention for a Compound of Formula I.

Another embodiment of the Invention is directed to a Compound of Formula I wherein $R^2$ is alkyl; and all other groups are as defined in the Summary of the Invention for a Compound of Formula I. In another embodiment, $R^2$ is methyl or ethyl in the Compound of Formula I; and all other groups are as defined in the Summary of the Invention for a Compound of Formula I.

Another embodiment of the Invention is directed to a Compound of Formula I wherein $R^4$ and $R^{4a}$ are hydrogen; and all other groups are as defined in the Summary of the Invention for a Compound of Formula I.

Another embodiment of the Invention is directed to a Compound of Formula I wherein $R^4$ is hydrogen and $R^{4a}$ is alkyl; and all other groups are as defined in the Summary of the Invention for a Compound of Formula I.

In another embodiment, the Compound of Formula I is that where $R^3$ is methylamino, ethylamino, n-propylamino, or isopropylamino; and all other groups are as defined in the Summary of the Invention for a Compound of Formula I.

In another embodiment, the Compound of Formula I is that where $R^3$ is methylamino; and all other groups are as defined in the Summary of the Invention for a Compound of Formula I.

Another embodiment of the Invention is directed to a Compound of Formula I wherein $R^4$ and $R^{4a}$ are alkyl; and all other groups are as defined in the Summary of the Invention for a Compound of Formula I.

In another embodiment, the Compound of Formula I is that where $R^3$ is dimethylamino, diethylamino, di-n-propylamino, or diisopropylamino; and all other groups are as defined in the Summary of the Invention for a Compound of Formula I.

In another embodiment, the Compound of Formula I is that where $R^3$ is dimethylamino; and all other groups are as defined in the Summary of the Invention for a Compound of Formula I.

In another embodiment, the invention is directed to a Compound of Formula I where $R^2$, $R^4$, and $R^{4a}$ are hydrogen; and $R^1$ is as defined in the Summary of the Invention for a Compound of Formula I.

In another embodiment, the invention is directed to a Compound of Formula I where $R^2$ is hydrogen, $R^4$ and $R^{4a}$ are alkyl, and $R^1$ is as defined in the Summary of the Invention for a Compound of Formula I.

In another embodiment, the invention is directed to a Compound of Formula I where $R^2$ is hydrogen, $R^4$ and $R^{4a}$ are methyl, and $R^1$ is as defined in the Summary of the Invention for a Compound of Formula I.

In another embodiment, the invention is directed to a Compound of Formula I where $R^2$ and $R^4$ are hydrogen, $R^{4a}$ is alkyl, and $R^1$ is as defined in the Summary of the Invention for a Compound of Formula I.

In one embodiment of the Invention (A1), the Compound of Formula I is that wherein $R^1$ is tetrahydrofuran-2-yl or tetrahydrofuran-3-yl; and all other groups are as defined in the Summary of the Invention for a Compound of Formula I. In another embodiment, the Compound of Formula I is that wherein $R^1$ is tetrahydrofuran-2-yl or tetrahydrofuran-3-yl and $R^2$ is hydrogen; and all other groups are as defined in the Summary of the Invention for a Compound of Formula I. In another embodiment, the Compound of Formula I is that wherein $R^1$ is tetrahydrofuran-2-yl or tetrahydrofuran-3-yl and $R^2$ is alkyl; and all other groups are as defined in the Summary of the Invention for a Compound of Formula I.

In another embodiment of the Invention (A2), the Compound of Formula I is that wherein $R^1$ is tetrahydrofuran-3-yl; and all other groups are as defined in the Summary of the Invention for a Compound of Formula I.

In another embodiment of the Invention (B1), the Compound of Formula I is according to Formula Ia

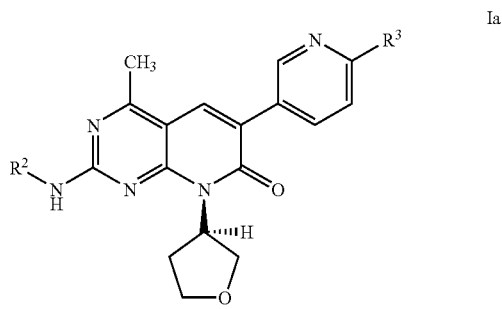

where $R^2$ and $R^3$ are as defined in the Summary of the Invention for a Compound of Formula I.

Another embodiment of the Invention (B2) is directed to a Compound of Formula Ia wherein $R^2$ is hydrogen; and all other groups are as defined in the Summary of the Invention for a Compound of Formula I.

Another embodiment of the Invention (B3) is directed to a Compound of Formula Ia wherein $R^2$ is alkyl; and all other groups are as defined in the Summary of the Invention for a Compound of Formula I. In another embodiment, $R^2$ is methyl or ethyl in the Compound of Formula Ia; and all other groups are as defined in the Summary of the Invention for a Compound of Formula I.

Another embodiment of the Invention (B4) is directed to a Compound of Formula Ia wherein $R^3$ is —$NR^4R^{4a}$ and $R^4$ and $R^{4a}$ are hydrogen; and all other groups are as defined in the Summary of the Invention for a Compound of Formula I.

Another embodiment of the Invention (B5) is directed to a Compound of Formula Ia wherein $R^3$ is —$NR^4R^{4a}$ and $R^4$ is hydrogen and $R^{4a}$ is alkyl; and all other groups are as defined in the Summary of the Invention for a Compound of Formula I.

In another embodiment (B6), the Compound of Formula Ia is that where $R^3$ is methylamino, ethylamino, n-propylamino, or isopropylamino; and all other groups are as defined in the Summary of the Invention for a Compound of Formula I.

In another embodiment (B7), the Compound of Formula Ia is that where $R^3$ is methylamino; and all other groups are as defined in the Summary of the Invention for a Compound of Formula I.

Another embodiment of the Invention (B8) is directed to a Compound of Formula Ia wherein $R^3$ is —$NR^4R^{4a}$ and $R^4$ and $R^{4a}$ are alkyl; and all other groups are as defined in the Summary of the Invention for a Compound of Formula I.

In another embodiment (B9), the Compound of Formula Ia is that where $R^3$ is dimethylamino, diethylamino, di-n-propylamino, or diisopropylamino; and all other groups are as defined in the Summary of the Invention for a Compound of Formula I.

In another embodiment (B10), the Compound of Formula Ia is that where $R^3$ is dimethylamino; and all other groups are as defined in the Summary of the Invention for a Compound of Formula I.

In another embodiment (B11), the invention is directed to a Compound of Formula Ia where $R^2$ is hydrogen and $R^3$ is —$NR^4R^{4a}$ where $R^4$ and $R^{4a}$ are hydrogen.

In another embodiment (B12), the invention is directed to a Compound of Formula Ia where $R^2$ is hydrogen and $R^3$ is —$NR^4R^{4a}$ where $R^4$ and $R^{4a}$ are alkyl.

In another embodiment (B13), the invention is directed to a Compound of Formula Ia where $R^2$ is hydrogen and $R^3$ is —$NR^4R^{4a}$ where $R^4$ and $R^{4a}$ are methyl.

In another embodiment (B14), the invention is directed to a Compound of Formula Ia where $R^2$ is hydrogen and $R^3$ is —$NR^4R^{4a}$ where $R^4$ is hydrogen and $R^{4a}$ is alkyl.

In another embodiment (B15), the invention is directed to a Compound of Formula Ia where $R^2$ is hydrogen and $R^3$ is —$NR^4R^{4a}$ where $R^4$ is hydrogen and $R^{4a}$ is methyl.

In another embodiment of the Invention (C1), the Compound of Formula I is according to Formula Ib

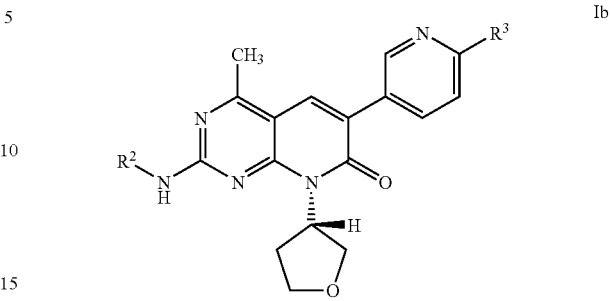

where $R^2$ and $R^3$ are as defined in the Summary of the Invention for a Compound of Formula I.

Another embodiment of the Invention (C2) is directed to a Compound of Formula Ib wherein $R^2$ is hydrogen; and all other groups are as defined in the Summary of the Invention for a Compound of Formula I.

Another embodiment of the Invention (C3) is directed to a Compound of Formula Ib wherein $R^2$ is alkyl; and all other groups are as defined in the Summary of the Invention for a Compound of Formula I. In another embodiment, $R^2$ is methyl or ethyl in the Compound of Formula Ib; and all other groups are as defined in the Summary of the Invention for a Compound of Formula I.

Another embodiment of the Invention (C4) is directed to a Compound of Formula Ib wherein $R^3$ is —$NR^4R^{4a}$ and $R^4$ and $R^{4a}$ are hydrogen; and all other groups are as defined in the Summary of the Invention for a Compound of Formula I.

Another embodiment of the Invention (C5) is directed to a Compound of Formula Ib wherein $R^3$ is —$NR^4R^{4a}$ and $R^4$ is hydrogen and $R^{4a}$ is alkyl; and all other groups are as defined in the Summary of the Invention for a Compound of Formula I.

In another embodiment (C6), the Compound of Formula Ib is that where $R^3$ is methylamino, ethylamino, n-propylamino, or isopropylamino; and all other groups are as defined in the Summary of the Invention for a Compound of Formula I.

In another embodiment (C7), the Compound of Formula Ib is that where $R^3$ is methylamino; and all other groups are as defined in the Summary of the Invention for a Compound of Formula I.

Another embodiment of the Invention (C8) is directed to a Compound of Formula Ib wherein $R^3$ is —$NR^4R^{4a}$ and $R^4$ and $R^{4a}$ are alkyl; and all other groups are as defined in the Summary of the Invention for a Compound of Formula I.

In another embodiment (C9), the Compound of Formula Ib is that where $R^3$ is dimethylamino, diethylamino, di-n-propylamino, or diisopropylamino; and all other groups are as defined in the Summary of the Invention for a Compound of Formula I.

In another embodiment (C10), the Compound of Formula Ib is that where $R^3$ is dimethylamino; and all other groups are as defined in the Summary of the Invention for a Compound of Formula I.

In another embodiment (C11), the invention is directed to a Compound of Formula Ib where $R^2$ is hydrogen and $R^3$ is —$NR^4R^{4a}$ where $R^4$ and $R^{4a}$ are hydrogen.

In another embodiment (C12), the invention is directed to a Compound of Formula Ib where $R^2$ is hydrogen and $R^3$ is —$NR^4R^{4a}$ where $R^4$ and $R^{4a}$ are alkyl.

In another embodiment (C13), the invention is directed to a Compound of Formula Ib where $R^2$ is hydrogen and $R^3$ is —$NR^4R^{4a}$ where $R^4$ and $R^{4a}$ are methyl.

In another embodiment (C14), the invention is directed to a Compound of Formula Ib where $R^2$ is hydrogen and $R^3$ is —$NR^4R^{4a}$ where $R^4$ is hydrogen and $R^{4a}$ is alkyl.

In another embodiment (C15), the invention is directed to a Compound of Formula Ib where $R^2$ is hydrogen and $R^3$ is —$NR^4R^{4a}$ where $R^4$ is hydrogen and $R^{4a}$ is methyl.

In another embodiment of the Invention (D1), the Compound of Formula I is that wherein $R^1$ is tetrahydropyran-2-yl, tetrahydropyran-3-yl, or tetrahydropyran-4-yl; and all other groups are as defined in the Summary of the Invention for a Compound of Formula I.

In another embodiment of the Invention (D2), the Compound of Formula I is that wherein $R^1$ is tetrahydropyran-3-yl; and all other groups are as defined in the Summary of the Invention for a Compound of Formula I.

In another embodiment of the Invention (E1), the Compound of Formula I is according to Formula Ic

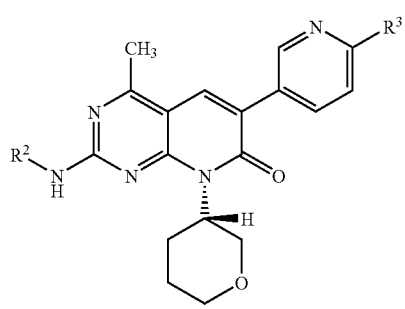

Ic where $R^2$ and $R^3$ are as defined in the Summary of the Invention for a Compound of Formula I.

Another embodiment of the Invention (E2) is directed to a Compound of Formula Ic wherein $R^2$ is hydrogen; and all other groups are as defined in the Summary of the Invention for a Compound of Formula I.

Another embodiment of the Invention (E3) is directed to a Compound of Formula Ic wherein $R^2$ is alkyl; and all other groups are as defined in the Summary of the Invention for a Compound of Formula I. In another embodiment, $R^2$ is methyl or ethyl in the Compound of Formula Ic; and all other groups are as defined in the Summary of the Invention for a Compound of Formula I.

Another embodiment of the Invention (E4) is directed to a Compound of Formula Ic wherein $R^3$ is —$NR^4R^{4a}$ and $R^4$ and $R^{4a}$ are hydrogen; and all other groups are as defined in the Summary of the Invention for a Compound of Formula I.

Another embodiment of the Invention (E5) is directed to a Compound of Formula Ic wherein $R^3$ is —$NR^4R^{4a}$ and $R^4$ is hydrogen and $R^{4a}$ is alkyl; and all other groups are as defined in the Summary of the Invention for a Compound of Formula I.

In another embodiment (E6), the Compound of Formula Ic is that where $R^3$ is methylamino, ethylamino, n-propylamino, or isopropylamino; and all other groups are as defined in the Summary of the Invention for a Compound of Formula I.

In another embodiment (E7), the Compound of Formula Ic is that where $R^3$ is methylamino; and all other groups are as defined in the Summary of the Invention for a Compound of Formula I.

Another embodiment of the Invention (E8) is directed to a Compound of Formula Ic wherein $R^3$ is —$NR^4R^{4a}$ and $R^4$ and $R^{4a}$ are alkyl; and all other groups are as defined in the Summary of the Invention for a Compound of Formula I.

In another embodiment (E9), the Compound of Formula Ic is that where $R^3$ is dimethylamino, diethylamino, di-n-propylamino, or diisopropylamino; and all other groups are as defined in the Summary of the Invention for a Compound of Formula I.

In another embodiment (E10), the Compound of Formula Ic is that where $R^3$ is dimethylamino; and all other groups are as defined in the Summary of the Invention for a Compound of Formula I.

In another embodiment (E11), the invention is directed to a Compound of Formula Ic where $R^2$ is hydrogen and $R^3$ is —$NR^4R^{4a}$ where $R^4$ and $R^{4a}$ are hydrogen.

In another embodiment (E12), the invention is directed to a Compound of Formula Ic where $R^2$ is hydrogen and $R^3$ is —$NR^4R^{4a}$ where $R^4$ and $R^{4a}$ are alkyl.

In another embodiment (E13), the invention is directed to a Compound of Formula Ic where $R^2$ is hydrogen and $R^3$ is —$NR^4R^{4a}$ where $R^4$ and $R^{4a}$ are methyl.

In another embodiment (E14), the invention is directed to a Compound of Formula Ic where $R^2$ is hydrogen and $R^3$ is —$NR^4R^{4a}$ where $R^4$ is hydrogen and $R^{4a}$ is alkyl.

In another embodiment (E15), the invention is directed to a Compound of Formula Ic where $R^2$ is hydrogen and $R^3$ is —$NR^4R^{4a}$ where $R^4$ is hydrogen and $R^{4a}$ is methyl.

In another embodiment of the Invention (F1), the Compound of Formula I is according to Formula Id

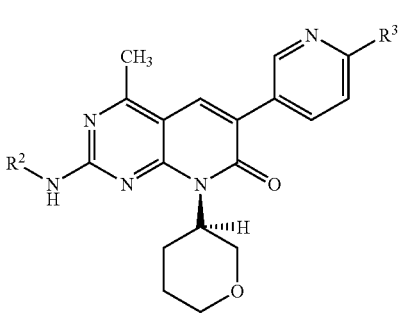

Id where $R^2$ and $R^3$ are as defined in the Summary of the Invention for a Compound of Formula I.

Another embodiment of the Invention (F2) is directed to a Compound of Formula Id wherein $R^2$ is hydrogen; and all other groups are as defined in the Summary of the Invention for a Compound of Formula I.

Another embodiment of the Invention (F3) is directed to a Compound of Formula Id wherein $R^2$ is alkyl; and all other groups are as defined in the Summary of the Invention for a Compound of Formula I. In another embodiment, $R^2$ is methyl or ethyl in the Compound of Formula Id; and all other groups are as defined in the Summary of the Invention for a Compound of Formula I.

Another embodiment of the Invention (F4) is directed to a Compound of Formula Id wherein $R^3$ is —$NR^4R^{4a}$ and $R^4$ and $R^{4a}$ are hydrogen; and all other groups are as defined in the Summary of the Invention for a Compound of Formula I.

Another embodiment of the Invention (F5) is directed to a Compound of Formula Id wherein $R^3$ is —$NR^4R^{4a}$ and $R^4$ is hydrogen and $R^{4a}$ is alkyl; and all other groups are as defined in the Summary of the Invention for a Compound of Formula I.

In another embodiment (F6), the Compound of Formula Id is that where $R^3$ is methylamino, ethylamino, n-propylamino, or isopropylamino; and all other groups are as defined in the Summary of the Invention for a Compound of Formula I.

In another embodiment (F7), the Compound of Formula Id is that where $R^3$ is methylamino; and all other groups are as defined in the Summary of the Invention for a Compound of Formula I.

Another embodiment of the Invention (F8) is directed to a Compound of Formula Id wherein $R^3$ is —$NR^4R^{4a}$ and $R^4$ and $R^{4a}$ are alkyl; and all other groups are as defined in the Summary of the Invention for a Compound of Formula I.

In another embodiment (F9), the Compound of Formula Id is that where $R^3$ is dimethylamino, diethylamino, di-n-propylamino, or diisopropylamino; and all other groups are as defined in the Summary of the Invention for a Compound of Formula I.

In another embodiment (F10), the Compound of Formula Id is that where $R^3$ is dimethylamino; and all other groups are as defined in the Summary of the Invention for a Compound of Formula I.

In another embodiment (F11), the invention is directed to a Compound of Formula Id where $R^2$ is hydrogen and $R^3$ is —$NR^4R^{4a}$ where $R^4$ and $R^{4a}$ are hydrogen.

In another embodiment (F12), the invention is directed to a Compound of Formula Id where $R^2$ is hydrogen and $R^3$ is —$NR^4R^{4a}$ where $R^4$ and $R^{4a}$ are alkyl.

In another embodiment (F13), the invention is directed to a Compound of Formula Id where $R^2$ is hydrogen and $R^3$ is —$NR^4R^{4a}$ where $R^4$ and $R^{4a}$ are methyl.

In another embodiment (F14), the invention is directed to a Compound of Formula Id where $R^2$ is hydrogen and $R^3$ is —$NR^4R^{4a}$ where $R^4$ is hydrogen and $R^{4a}$ is alkyl.

In another embodiment (F15), the invention is directed to a Compound of Formula Id where $R^2$ is hydrogen and $R^3$ is —$NR^4R^{4a}$ where $R^4$ is hydrogen and $R^{4a}$ is methyl.

In another embodiment of the Invention (G1), the Compound of Formula I is according to Formula Ie

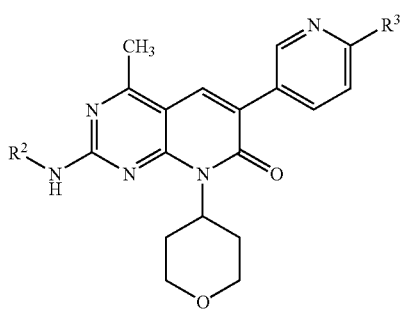

Ie where $R^2$ and $R^3$ are as defined in the Summary of the Invention for a Compound of Formula I.

In another embodiment of the Invention (G2), the Compound of Formula I is according to Formula Ie where $R^2$ is hydrogen; and all other groups are as defined in the Summary of the Invention for a Compound of Formula I.

Another embodiment of the Invention (G3) is directed to a Compound of Formula I according to Formula Ie where $R^2$ is alkyl; and all other groups are as defined in the Summary of the Invention for a Compound of Formula I. In another embodiment, the Compound of Formula Ie is that where $R^2$ is methyl or ethyl; and all other groups are as defined in the Summary of the Invention for a Compound of Formula I.

Another embodiment of the Invention (G4) is directed to a Compound of Formula I according to Formula Ie wherein $R^3$ is —$NR^4R^{4a}$ and $R^4$ and $R^{4a}$ are hydrogen; and all other groups are as defined in the Summary of the Invention for a Compound of Formula I.

Another embodiment of the Invention (G5) is directed to a Compound of Formula I according to Formula Ie wherein $R^3$ is —$NR^4R^{4a}$ and $R^4$ is hydrogen and $R^{4a}$ is alkyl; and all other groups are as defined in the Summary of the Invention for a Compound of Formula I.

In another embodiment (G6), the Compound of Formula I is according to Formula Ie where $R^3$ is methylamino, ethylamino, n-propylamino, or isopropylamino; and all other groups are as defined in the Summary of the Invention for a Compound of Formula I.

In another embodiment (G7), the Compound of Formula I is according to Formula Ie where $R^3$ is methylamino; and all other groups are as defined in the Summary of the Invention for a Compound of Formula I.

Another embodiment of the Invention (G8) is directed to a Compound of Formula I according to Formula Ie wherein $R^3$ is —$NR^4R^{4a}$ and $R^4$ and $R^{4a}$ are alkyl; and all other groups are as defined in the Summary of the Invention for a Compound of Formula I.

In another embodiment (G9), the Compound of Formula I is according to Formula Ie where $R^3$ is dimethylamino, diethylamino, di-n-propylamino, or diisopropylamino; and all other groups are as defined in the Summary of the Invention for a Compound of Formula I.

In another embodiment (G10), the Compound of Formula I is according to Formula Ie where $R^3$ is dimethylamino; and all other groups are as defined in the Summary of the Invention for a Compound of Formula I.

In another embodiment (G11), the invention is directed to a Compound of Formula I according to Formula Ie where $R^2$ is hydrogen, and $R^3$ is —$NR^4R^{4a}$ where $R^4$ and $R^{4a}$ are hydrogen.

In another embodiment (G12), the invention is directed to a Compound of Formula I according to Formula Ie where $R^2$ is hydrogen, and $R^3$ is —$NR^4R^{4a}$ where $R^4$ and $R^{4a}$ are alkyl.

In another embodiment (G13), the invention is directed to a Compound of Formula I according to Formula Ie where $R^2$ is hydrogen, and $R^3$ is —$NR^4R^{4a}$ where $R^4$ and $R^{4a}$ are methyl.

In another embodiment (G14), the invention is directed to a Compound of Formula I according to Formula Ie where $R^2$ is hydrogen, and $R^3$ is —$NR^4R^{4a}$ where $R^4$ is hydrogen and $R^{4a}$ is alkyl.

In another embodiment (G15), the invention is directed to a Compound of Formula I according to Formula Ie where $R^2$ is hydrogen, and $R^3$ is —$NR^4R^{4a}$ where $R^4$ is hydrogen and $R^{4a}$ is methyl.

Another embodiment (K) of the invention is directed to a pharmaceutical composition which comprises a compound of Formula I optionally as a single stereoisomer or mixture of stereoisomers thereof, and additionally optionally as a pharmaceutically acceptable salt thereof, and a pharmaceutically acceptable carrier, excipient, or diluent. In another embodiment, the Compound of Formula I is according to any of the above embodiments.

Any of the following embodiments can be practiced with any of the above embodiments. All such combinations of embodiments is within the scope of the Invention.

Another embodiment (H) of the Invention is a method of treating disease, disorder, or syndrome where the disease is associated with uncontrolled, abnormal, and/or unwanted cellular activities effected directly or indirectly by PI3Kα and/or mTOR which method comprises administering to a human in need thereof a therapeutically effective amount of a compound of Formula I optionally as a single stereoisomer or mixture of stereoisomers thereof, additionally optionally as a pharmaceutically acceptable salt thereof, or a pharmaceutical composition thereof. In another embodiment, the Compound of Formula I is according to Formula Ia. In another embodiment, the Compound of Formula I is according to Formula Ib. In another embodiment, the Compound of Formula I is according to Formula Ic. In another embodiment, the Compound of Formula I is according to Formula Id. In another embodiment, the Compound of Formula I is according to Formula Ie. In another embodiment, the Compound of Formula I is selected from Table 2.

Another embodiment (J) of the invention is directed to a method of treating a disease, disorder, or syndrome which method comprises administering to a patient a therapeutically effective amount of a compound of Formula I optionally as a single stereoisomer or mixture of stereoisomers thereof, and additionally optionally as a pharmaceutically acceptable salt thereof, or a pharmaceutical composition comprising a therapeutically effective amount of a compound of Formula I optionally as a single stereoisomer or mixture of stereoisomers thereof, additionally optionally as a pharmaceutically acceptable salt thereof, and a pharmaceutically acceptable carrier, excipient, or diluent. In another embodiment (J1) of embodiment (J), the disease is cancer. In another embodiment (J2) of embodiment (J1), the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), multiple myeloma, or thyroid carcinoma. In another embodiment (J3) of embodiment (J2), the cancer is ovarian cancer, cervical cancer, endometrial cancer, breast cancer, colon cancer, rectal cancer, non-small cell lung cancer, prostate carcinoma, or glioblastoma. In another embodiment (J4) of embodiment (J), (J1), (J2), or (J3), the Compound of Formula I is according to Formula Ia. In another embodiment (J5) of embodiment (J), (J1), (J2), or (J3), the Compound of Formula I is according to Formula Ib. In another embodiment (J6) of embodiment (J), (J1), (J2), or (J3), the Compound of Formula I is according to Formula Ic. In another embodiment (J7) of embodiment (J), (J1), (J2), or (J3), the Compound of Formula I is according to Formula Id. In another embodiment (J8) of embodiment (J), (J1), (J2), or (J3), the Compound of Formula I is according to Formula Ie. In another embodiment (J9) of embodiment (J), (J1), (J2), or (J3), the Compound of Formula I is selected from Table 2.

Compounds in Table 1 are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Names were generated using ACD/Labs naming software 8.00 release, product version 8.08.

TABLE 1

| Ex | Structure | Name |
|----|-----------|------|
| 1 | 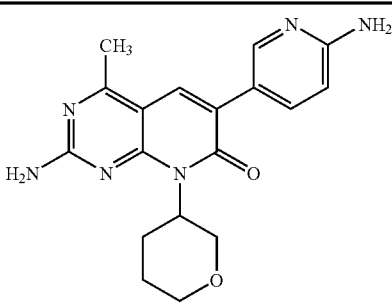 | 2-amino-6-(6-aminopyridin-3-yl)-4-methyl-8-(tetrahydro-2H-pyran-3-yl)pyrido[2,3-d]pyrimidin-7(8H)-one |
| 2 | 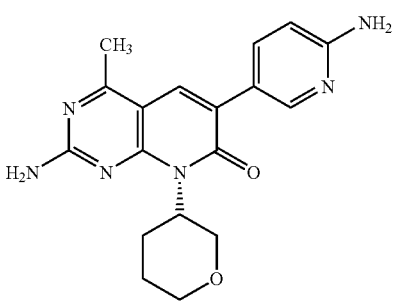 | 2-amino-6-(6-aminopyridin-3-yl)-4-methyl-8-[(3S)-tetrahydro-2H-pyran-3-yl]pyrido[2,3-d]pyrimidin-7(8H)-one |

TABLE 1-continued

| Ex | Structure | Name |
|---|---|---|
| 3 | 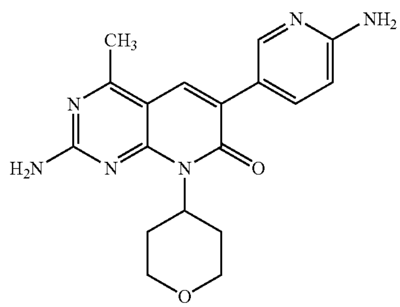 | 2-amino-6-(6-aminopyridin-3-yl)-4-methyl-8-(tetrahydro-2H-pyran-4-yl)pyrido[2,3-d]pyrimidin-7(8H)-one |
| 4 | 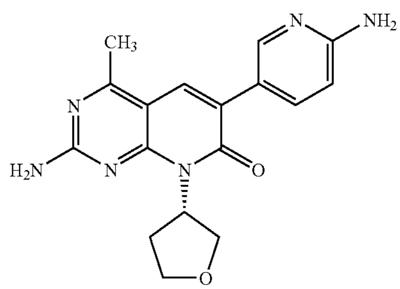 | 2-amino-6-(6-aminopyridin-3-yl)-4-methyl-8-[(3S)-tetrahydrofuran-3-yl]pyrido[2,3-d]pyrimidin-7(8H)-one |
| 5 | 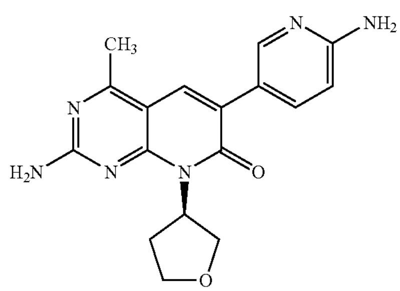 | 2-amino-6-(6-aminopyridin-3-yl)-4-methyl-8-[(3R)-tetrahydrofuran-3-yl]pyrido[2,3-d]pyrimidin-7(8H)-one |
| 6 | 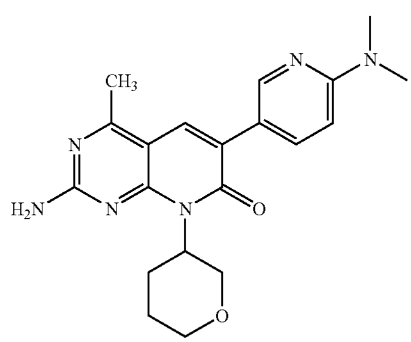 | 2-amino-6-[6-(dimethylamino)pyridin-3-yl]-4-methyl-8-(tetrahydro-2H-pyran-3-yl)pyrido[2,3-d]pyrimidin-7(8H)-one |
| 7 | 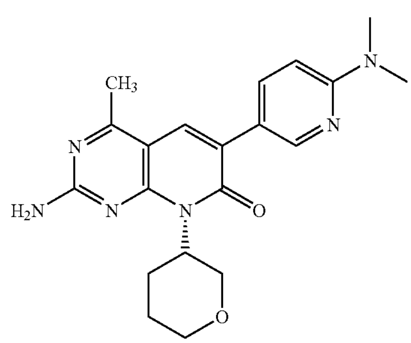 | 2-amino-6-[6-(dimethylamino)pyridin-3-yl]-4-methyl-8-[(3S)-tetrahydro-2H-pyran-3-yl]pyrido[2,3-d]pyrimidin-7(8H)-one |

TABLE 1-continued

| Ex | Structure | Name |
|----|-----------|------|
| 8 | 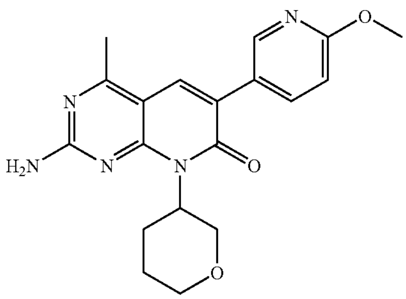 | 2-amino-6-(6-methoxypyridin-3-yl)-4-methyl-8-(tetrahydro-2H-pyran-3-yl)pyrido[2,3-d]pyrimidin-7(8H)-one |

TABLE 2

Compounds of the Invention

| Structure | P13K-α, β (nM) | mTOR (nM) | pS6 (S240/S244) PC-3 cell line (nM) | MCF-7 2-day Proliferation (nM) | PC-3 2-day Proliferation (nM) | Mouse Liver Microsome Oxidation (%) |
|---|---|---|---|---|---|---|
| Cmpd 1 | 5.5, 52.1 | 2.6 | 15.8 | 97.8 | 150.4 | 15.2 |
| Cmpd 2 | 7.3, 60.8 | 3 | 25.6 | 150.8 | 297.2 | 6.6 |
| Cmpd 3 | 9, 19.8 | 3.2 | 25 | 152.1 | 279.5 | −7.8 |

TABLE 2-continued
Compounds of the Invention
| | P13K-α, β (nM) | mTOR (nM) | pS6 (S240/S244) PC-3 cell line (nM) | MCF-7 2-day Proliferation (nM) | PC-3 2-day Proliferation (nM) | Mouse Liver Microsome Oxidation (%) |
|---|---|---|---|---|---|---|
| 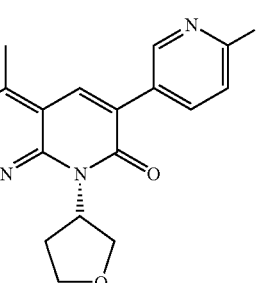<br>Cmpd 4 | 15.5, 16.7 | 5.5 | 36.6 | 376.7 | 400.8 | 1.7 |
| 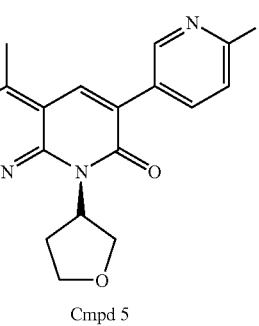<br>Cmpd 5 | <9.1, 34 | 2.5 | 18.5 | 217.3 | 497.2 | −8.2 |
TABLE 3
Comparative Compounds
| | P13K-α, β (nM) | mTOR (nM) | pS6 (S240/S244) PC-3 cell line (nM) | MCF-7 2-day Proliferation (nM) | PC-3 2-day Proliferation (nM) | Mouse Liver Microsome Oxidation (%) |
|---|---|---|---|---|---|---|
| 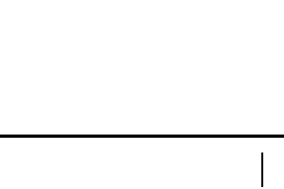<br>Cmpd 6 | 13.5, 204.9 | 6.1 | 96.2 | 151.1 | 740.9 | 31.2 |

TABLE 3-continued

Comparative Compounds

| | PI3K-α, β (nM) | mTOR (nM) | pS6 (S240/S244) PC-3 cell line (nM) | MCF-7 2-day Proliferation (nM) | PC-3 2-day Proliferation (nM) | Mouse Liver Microsome Oxidation (%) |
|---|---|---|---|---|---|---|
| Cmpd 7 | 9.2, 470.9 | 5.8 | 71.7 | 247 | 1330 | 41.3 |
| Cmpd 8 | 2.8, 6.8 | 6.8 | 40.8 | 217.9 | 468.6 | 45.6 |

Compounds in Table 2 and 3 are very potent inhibitors of both PI3K and mTOR in biochemical assays (see Biological Examples 1 and 2), in cell-based assays where PI3K signaling is activated (see Biological Example 3), and in cellular proliferation assays (see Biological Example 4). In addition to being very potent, the Compounds in Table 2, in contrast to those in Table 3, show unexpected results when tested in a mouse microsomal oxidation assay (see Biological Example 5). Activity in this assay is an indicator of metabolic instability and the assay is used as a tool to determine druggability of a compound. The higher the percent metabolism in this assay, the more the compound is degraded by the liver microsomes and the greater the risk the compound may be extensively metabolized when administered to animals or humans. The Compounds of the Invention as depicted in Table 2 demonstrate no metabolic liabilities or markedly less in mouse liver microsomes when compared to those in Table 3.

General Administration

In one aspect, the invention provides pharmaceutical compositions comprising a compound according to the invention and a pharmaceutically acceptable carrier, excipient, or diluent. In certain other specific embodiments, administration is by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage fauns, such as for example, tablets, suppositories, pills, soft elastic and hard gelatin capsules, powders, solutions, suspensions, or aerosols, or the like, specifically in unit dosage forms suitable for simple administration of precise dosages.

The compositions will include a conventional pharmaceutical carrier or excipient and a compound of the invention as the/an active agent, and, in addition, may include carriers and adjuvants, etc.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts or solvates, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Representative pharmaceutical formulations containing a compound of Formula I are described below in the Pharmaceutical Composition Examples.

General Synthesis

Compounds of this invention can be made by the synthetic procedures described below. The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, $4^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., more specifically from about 0° C. to about 125° C. and more specifically at about room (or ambient) temperature, e.g., about 20° C. Unless otherwise stated (as in the case of an hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of Formula I that may be prepared through the syntheses described herein may exist as single stereoisomers, racemates, mixtures of enantiomers, and mixtures of diastereomers. All such single stereoisomers and mixtures are intended to be within the scope of this invention.

Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention. In particular, imidazol-5-yl and pyrazol-5-yl each can also exist in their respective tautomeric forms imidazol-4-yl and pyrazol-3-yl. Regardless of which structure or which terminology is used, each tautomer is included within the scope of the Invention.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The chemistry for the preparation of the compounds of this invention is known to those skilled in the art. In fact, there may be more than one process to prepare the compounds of the invention. The following examples illustrate but do not limit the invention. Compounds of the Invention which are not specifically described below can be prepared using the procedures described herein and also procedures known to one of ordinary skill in the art including those described in WO 2007/044813 and WO 2008/127712 which are both herein incorporated by reference. All references cited herein are incorporated by reference in their entirety.

A Compound of Formula I where $R^2$ is hydrogen and $R^1$ and $R^3$ are as defined in the Summary of the Invention for a Compound of Formula I can be prepared as described in Scheme 1.

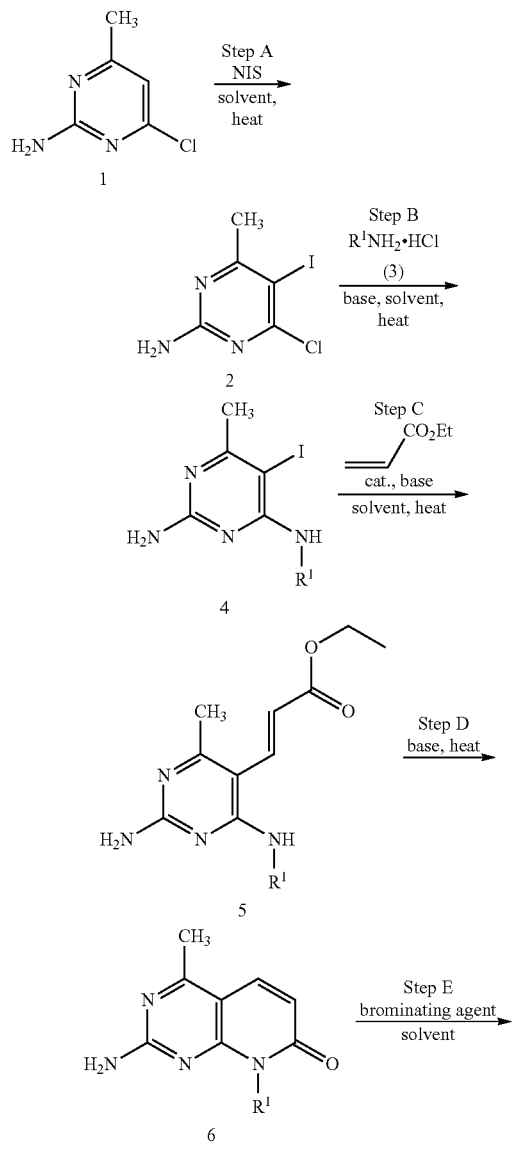

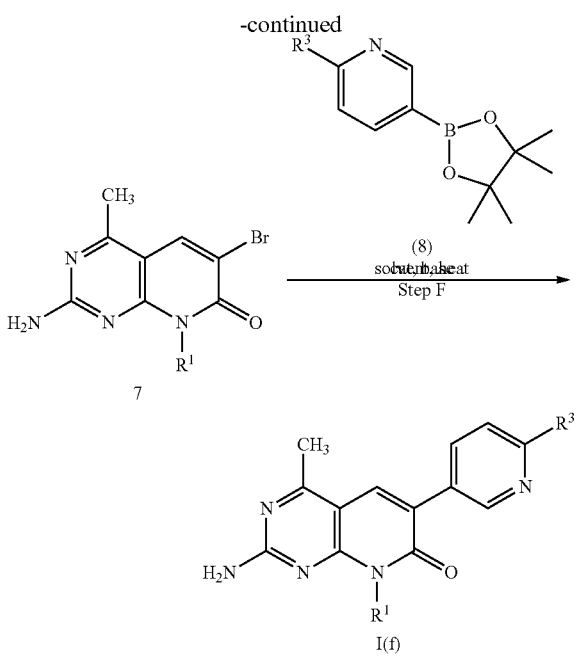

Step A: Commercially-available intermediate 1 is treated with an iodinating agent, such as iodine monochloride or iodine monobromide, in a solvent such as methanol at around 0° C. and allowed to react at room temperature for approximately overnight or less as needed for the reaction to go to completion to form 2. After completion the residue can be triturated with acetone. Alternatively, after completion, the reaction mixture can be poured into 0.2 N sodium thiosulfate to quench excess iodine. Alternatively, Intermediate 2 can be prepared by treating with N-iodosuccinimide in a solvent such as acetonitrile and/or methanol with heating.

Step B: An intermediate of formula 4 is prepared by reacting a intermediate of formula 2 with a commercially-available primary amine $R^1NH_2$ (as the free amine or salt thereof, such as an HCl salt) in solvents, such as water and such as a water/ethanol mixture, in the presence of a base such as TEA, and by heating the reaction.

Alternatively, Steps A and B can be conducted in reverse order to yield the intermediate of formula 4.

Step C: Intermediate 4 is then reacted in a solvent, such as DMA or DMF, with ethyl acrylate in the presence of a base, such as triethylamine, and in the presence of a catalyst, such as $Pd(OAc)_2$ in the presence of (+)BINAP or a catalyst such as $(Pd(PPh_3)_4$. The reaction is heated to approximately 95-100° C. and allowed to react for approximately overnight or less as needed for the reaction to go to completion to form 5. 5 is then optionally purified by column chromatography.

6 is prepared by treating 5 with DBU optionally in the presence of a base such as DIEA at about room temperature. The reaction mixture is then heated to reflux or about 170° C. and allowed to proceed until completion, approximately 5-15 h. After evaporation of the solvent, the residue is triturated with acetone and collected by filtration to yield 6. Alternatively, the reaction is allowed to cool to room temperature and then purified directly by column chromatography.

Intermediate 7 is prepared by reacting 6 with a brominating agent such as $Br_2$ in a solvent such as DCM at about room temperature. The reaction mixture is then stirred for approximately three hours to overnight. The resulting product is filtered and then suspended in a solvent such as DCM and treated with a base such as triethylamine. The organic layers are washed with water and dried over a drying agent such as Na₂SO₄ to yield 7. Alternatively, after completion, the reaction mixture is partially concentrated and acetone is added, followed by concentrating and precipitating in a solvent such as ethyl acetate which can then be collected by filtration to yield 7.

A Suzuki coupling can be performed on 7 using a boronic acid (or ester) of formula 8, which is commercially available or can be prepared using procedures known to one of ordinary skill in the art, in a solvent such as a DME-H₂O mixture or such as a dioxane-H₂O mixture, in the presence of a catalyst such as Pd(dpppf)₂ or Pd(PPh₃)₄ and in the presence of a base such as triethylamine or K₂CO₃. The reaction mixture is heated to reflux or about 95-100° C. for approximately 3 h. After cooling to room temperature, the reaction mixture is partitioned with water and ethyl acetate. After separation, the organic layer is dried over a drying agent such as Na₂SO₄ to yield a Compound of Formula I(f).

Alternatively, a Stille coupling can be performed on 7 (either as the free base or as a salt such as an HBr salt) using a tin reagent of formula

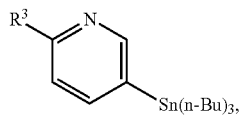

in a solvent such as toluene, in the presence of a catalyst such as Pd(PPh₃)₄, and optionally in the presence of a base such as triethylamine of Hunig's base. The reaction is heated at about 80-110° C. for about four hours. After cooling to room temperature, the reaction mixture can be purified by column chromatography to yield a Compound of Formula I(f). Alternatively, after cooling to room temperature, 40% KF on alumina is added. The mixture is then filtered through Celite to remove the alumina and the Celite is then washed with a solvent such as ethyl acetate. The resulting filtrate can then be washed with 1 M aqueous KF and brine. The organic layers are dried over a drying agent such as MgSO₄, filtered and concentrated in vacuo. The residue can then be triturated with methylene chloride and hexane to yield a Compound of Formula I(f).

Alternatively, a Compound of Formula I where R¹, R², and R³ are as defined in the Summary of the Invention for a Compound of Formula I can be prepared as described in Scheme 2.

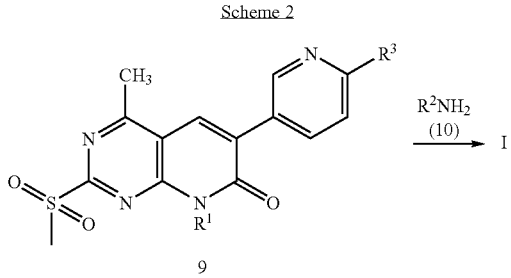

Intermediate 9, which can be prepared using procedures described in WO 2007/044813, is treated with an intermediate of formula R²NH₂, which is commercially available, in a solvent such as dioxane and stirred at room temperature for approximately overnight to yield a Compound of Formula I.

SYNTHETIC EXAMPLES

Example 1

Cmpd 3

2-amino-6-(6-aminopyridin-3-yl)-4-methyl-8-(tetrahydro-2H-pyran-4-yl)pyrido[2,3-d]pyrimidin-7(8H)-one

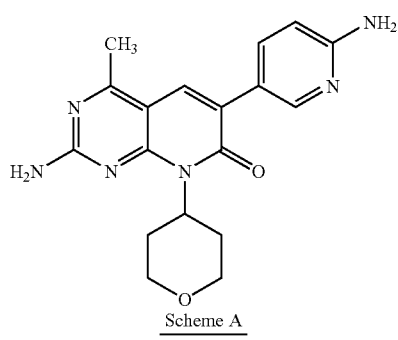

Scheme A

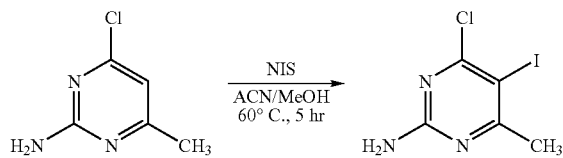

To a suspension of 2-amino-4-chloro-6-methylpyrimidine (10.0 g, 70.0 mmol) in acetonitrile (100 mL) and MeOH (140 mL) was added N-iodosuccinimide (24.0 g, 105.0 mmol) at room temperature. The reaction was heated to 60° C. and stirred for 5 h under nitrogen and was then cooled to room temperature. About 80% of the solvent was evaporated under reduced pressure and the mixture was diluted with diethyl ether (200 mL) to afford 4-chloro-5-iodo-6-methylpyrimidin-2-amine as a fine crystal (yield: 15.70 g, 83.2%). LC/MS: calculated for C₅H₅ClN₃ (270.47). found: 272.65 (M+2). HPLC analytical purity: 97.3%.

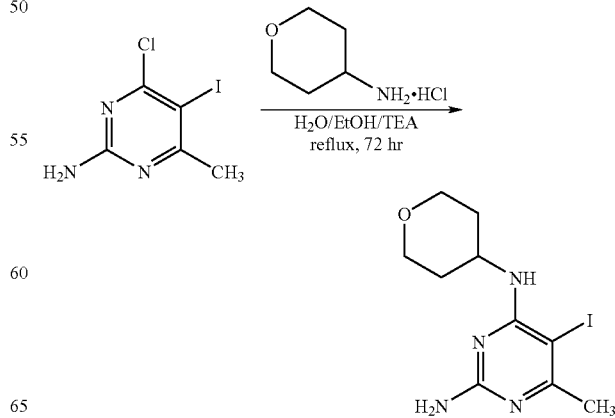

To a suspension of 4-chloro-5-iodo-6-methylpyrimidin-2-amine (16.0 g, 59.3 mmol) in EtOH (200 mL) and H$_2$O (250 mL) was added triethylamine (30.0 mL, 207.5 mmol) and 4-aminotetrahydropyran HCl salt (9.75 g, 71.2 mmol) successively. The reaction was heated to reflux, stirred for 72 h, and then cooled to RT. About 80% of the solvent was evaporated under reduced pressure. The mixture was partitioned between ethyl acetate and H$_2$O. The organic layer was dried over anhydrous sodium sulfate and concentrated in vacuo to afford the crude product. The product was purified by a flash chromatography (50% ethyl acetate/hexanes to 100% ethyl acetate) to afford 5-iodo-6-methyl-N$^4$-(tetrahydro-2H-pyran-4-yl)pyrimidine-2,4-diamine as a light yellow crystal (yield: 10.23 g, 51.7%). LC/MS: calculated for C$_{10}$H$_{15}$IN$_4$O (334.03). found: 335.08 (MH$^+$). HPLC analytical purity: >99.0%.

Scheme C

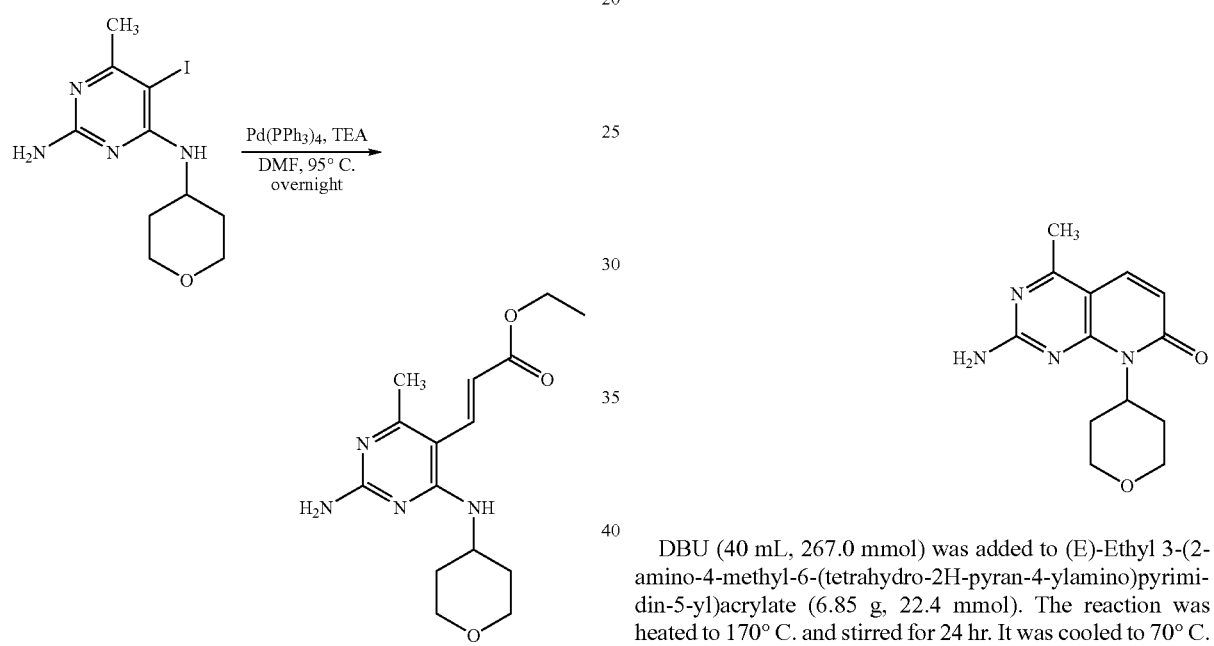

To a solution of 5-iodo-6-methyl-N$^4$-(tetrahydro-2H-pyran-4-yl)pyrimidine-2,4-diamine (10.0 g, 30.0 mmol) in DMF (200 mL) was added triethylamine (12.50 mL, 90.0 mmol) and ethyl acrylate (9.80 mL, 90.0 mmol) successively at room temperature. The reaction was purged with nitrogen for 5 min. and Pd(PPh$_3$)$_4$ (10 mol %, 3.50 g) was added. The reaction was heated to 95° C., stirred for overnight under nitrogen, and then cooled to room temperature. Nearly all DMF was evaporated under reduced pressure. The reaction was poured into ethyl acetate (500 mL) and H$_2$O (300 mL). The organic layer collected and dried over anhydrous sodium sulfate, and concentrated in vacuo to afford the crude product. The product was purified by a flash chromatography (70% ethyl acetate/hexanes to 10% EtOH/ethyl acetate) to afford (E)-ethyl 3-(2-amino-4-methyl-6-(tetrahydro-2H-pyran-4-ylamino)pyrimidin-5-yl)acrylate, as a light yellow semicrystal (yield: 6.85 g, 75.0%). LC/MS: calculated for C$_{15}$H$_{22}$N$_4$O$_3$ (306.17). found: 307.2 (MH$^+$). HPLC analytical purity: >97.0%.

Scheme D

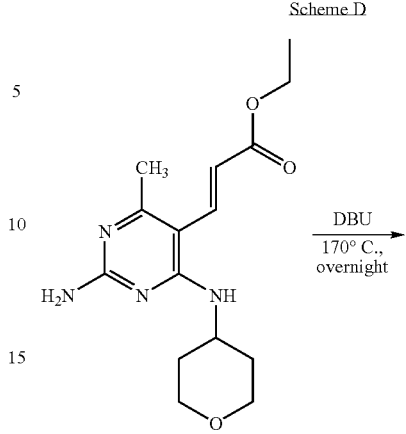

DBU (40 mL, 267.0 mmol) was added to (E)-Ethyl 3-(2-amino-4-methyl-6-(tetrahydro-2H-pyran-4-ylamino)pyrimidin-5-yl)acrylate (6.85 g, 22.4 mmol). The reaction was heated to 170° C. and stirred for 24 hr. It was cooled to 70° C. and followed with addition of H$_2$O (100 mL) to precipitate crystal. The mixture was slowly cooled to room temperature over 3 h. The brown crystal was collected and washed with H$_2$O yielding the desired product, 2-amino-4-methyl-8-(tetrahydro-2H-pyran-4-yl)pyrido[2,3-d]pyrimidin-7(8H)-one (yield: 3.0 g, 51.5%). LC/MS: calculated for C$_{13}$H$_{16}$N$_4$O$_2$ (260.13). found: 261.2 (MH$^+$). HPLC analytical purity: >95%.

Scheme E

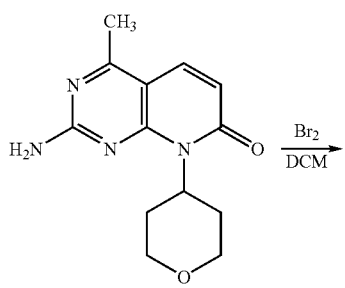

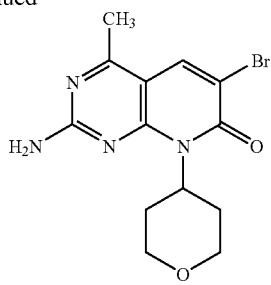

To a suspension of 2-amino-4-methyl-8-(tetrahydro-2H-pyran-3-yl) pyrido[2,3-d]pyrimidin-7(8H)-one (3.0 g, 11.5 mmol) in dichloromethane (100 mL) was added bromine (0.71 mL, 13.9 mmol) dropwise. This reaction was stirred for 3 h at room temperature. The solvent was evaporated under reduced pressure until approximately 80% of solvent had been removed. Ethyl acetate (100 mL) was then added to afford the product, 2-amino-6-bromo-4-methyl-8-(tetrahydro-2H-pyran-4-yl)pyrido[2,3-d]pyrimidin-7(8H)-one HBr salt (yield: 4.50 g, 92.7%) as light yellow crystal. LC/MS: Calculated for $C_{13}H_{15}BrN_4O_2$ (339.04). Found: 341.1 (M+2). HPLC analytical purity: >97%.

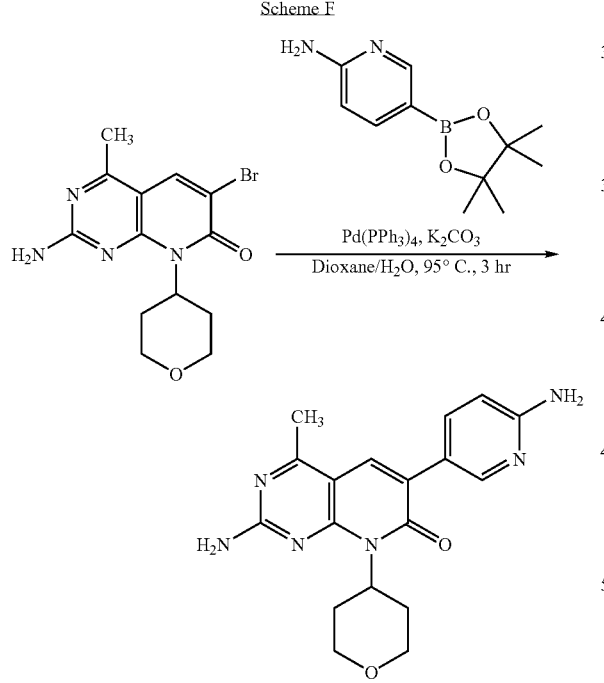

Scheme F

To a suspension of 2-amino-6-bromo-4-methyl-8-(tetrahydro-2H-pyran-4-yl)pyrido[2,3-d]pyrimidin-7(8H)-one HBr salt (4.50 g, 10.7 mmol) in dioxane (100 mL) and $H_2O$ (35 mL) were added 2-aminopyridine-5-boronic acid pinacol ester (3.55 g, 16.06 mmol) and $K_2CO_3$ (4.50 g, 32.1 mmol). The reaction was purged with nitrogen for 5 min and $Pd(PPh_3)_4$ (1.24 g, 10 mol %) was added. It was heated to 95° C. and stirred for 3 h under nitrogen. HPLC analysis after 3 h revealed no starting material remaining. Stirring was stopped and this reaction mixture was poured into ethyl acetate (200 mL) and $H_2O$ (100 mL). The organic layer was evaporated approximately to 50% of its volume and was slowly cooled to room temperature over about 3 h to precipitate the crude product. The solid was collected by filtration and washed with water (50 mL) and ethyl acetate (50 mL) to yield 2.5 g of crude product as a yellow solid.

To the solid crude product (3.0 g) was added 1,4-dioxane (380 mL) and deionized water (91 mL), and heated above 70° C. to dissolve the freebase. To the hot solution was added 146 mg of Si-SPM3 scavenging resin (8% by weight, PhosphonicS Ltd, Oxford, UK) and heated to 85-90° C. for 1 h. The reaction mixture was filtered while hot and the flask and the filter were rinsed with 1,4-dioxane (20 mL). The filtrate was concentrated under reduced pressure until about 70% of the solvent had been removed. The suspension was cooled to room temperature, over about 4 h, and the precipitated solid was collected by vacuum filtration, washed with ethyl acetate (30 mL) and dried in a high vacuum overnight to afford the product, 2-amino-6-(6-aminopyridin-3-yl)-4-methyl-8-(tetrahydro-2H-pyran-4-yl)pyrido[2,3-d]pyrimidin-7(8H)-one (yield: 1.50 g, 39.8%) as light yellow crystal. LC/MS: calculated for $C_{18}H_{20}N_6O_2$ (352.4). found: 353.04 (MH$^+$). HPLC analytical purity: >99%. $^1$H NMR (DMSO-d$_6$, 400 MHz); δ 8.21 (s, 1H), 7.83 (s, 1H), 7.70 (d, 1H), 7.10 (s, 2H), 6.41 (d, 1H), 6.02 (s, 2H), 5.70 (m, 1H), 4.01 (m, 2H), 3.40 (m, 3H), 2.95 (m, 2H), 2.57 (s, 3H), 1.50 (m, 2H).

Example 2

Cmpd 5

2-amino-6-(6-aminopyridin-3-yl)-4-methyl-8-[(3R)-tetrahydrofuran-3-yl]pyrido[2,3-d]pyrimidin-7(8H)-one

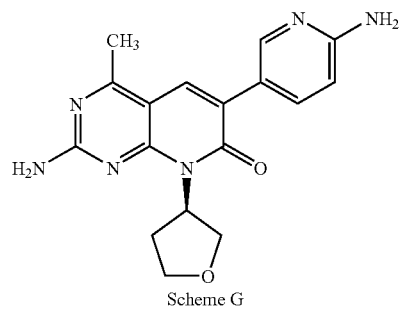

Scheme G

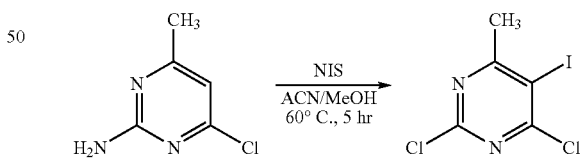

To a solution of 2-amino-4-chloro-6-methylpyrimidine (Aldrich, 10 g, 70 mmol) in acetonitrile (100 mL) and MeOH (140 mL) was added N-iodosuccinimide (Aldrich, 24 g, 105 mmol) at room temperature. The reaction mixture was heated to 60° C. for 5 h under a nitrogen atmosphere. After the reaction was complete, by monitoring LC/MS, it was allowed to cool to room temperature. The reaction mixture was put on a rotary evaporator and the solvent was evaporated to the half of its original volume. A precipitate was formed by addition of diethyl ether (200 mL). The precipitate was collected by vacuum filtration to afford (15.7 g, 83% yield) of the 4-chloro-5-iodo-6-methylpyrimidin-2-amine; MS (EI) for C₅H₅ClIN₃ (272.65, M+2): analytical HPLC purity >97%.

Scheme H

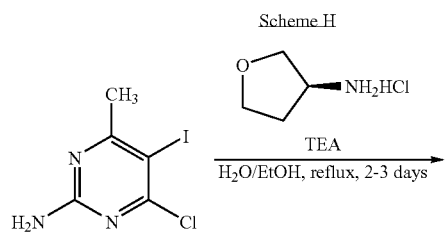

A mixture of 4-chloro-5-iodo-6-methylpyrimidin-2-amine (7.03 g, 26.08 mmol), (R)-tetrahydrofuran-3-amine hydrochloride (Milestone PharmTech, 3.90 g, 31.3 mmol) and triethylamine (9.236 g, 91.3 mmol) in EtOH (150 mL) and water (50 mL) was refluxed for 2-3 days. The reaction was monitored by LC/MS. After completion, the reaction mixture was cooled to ambient temperature and partitioned between 150 mL of ethyl acetate and 200 mL of water. The aqueous layer was extracted by ethyl acetate 3 times. The combined organic layers were dried (MgSO₄) and concentrated under reduced pressure. Recrystallization of the residue from ethyl acetate afforded (R)-5-iodo-6-methyl-N⁴-(tetrahydrofuran-3-yl)pyrimidine-2,4-diamine (4.53 g, 54% yield). MS (EI) for C₉H₁₃IN₄O: 321.0 (MH⁺).

Scheme J

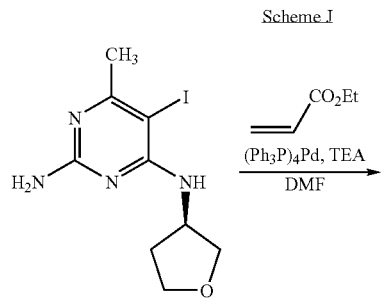

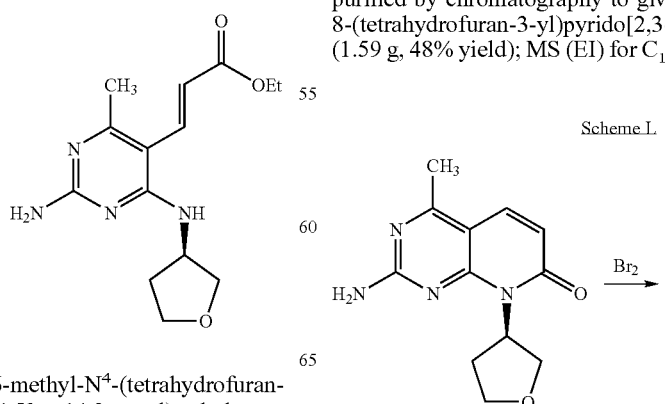

To a solution of (R)-5-iodo-6-methyl-N⁴-(tetrahydrofuran-3-yl)pyrimidine-2,4-diamine (4.53 g, 14.2 mmol), ethyl acrylate (4.25 g, 42.5 mmol) and triethylamine (4.30 g, 42.5 mmol) in DMF (150 mL) was added Pd(PPh₃)₄ (1.635 g, 10 mol %) under nitrogen at room temperature. The resulting mixture was heated to 95° C. for 18 h under a nitrogen atmosphere. After the reaction was complete by LC/MS, the resulting mixture was concentrated under reduced pressure and directly subjected to column chromatography purification to give (R,E)-ethyl 3-(2-amino-4-methyl-6-(tetrahydrofuran-3-ylamino)pyrimidin-5-yl)acrylate (3.90 g, 94% yield). MS (EI) for C₁₄H₂₀N₄O: 293.2 (MH⁺).

Scheme K

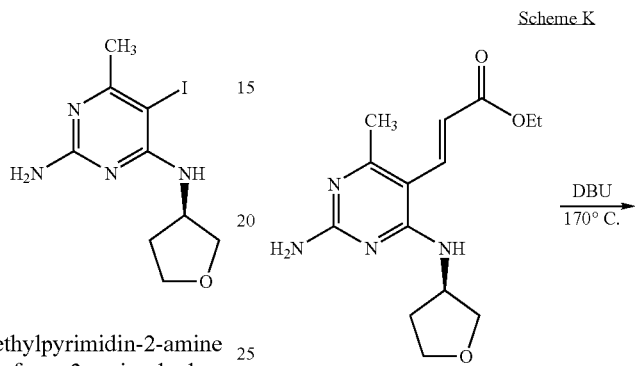

To a flask were added DBU (20 mL) and (R,E)-ethyl 3-(2-amino-4-methyl-6-(tetrahydrofuran-3-ylamino)pyrimidin-5-yl)acrylate (3.9 g, 13.4 mmol). The reaction mixture was stirred at 170° C. for 24 h under nitrogen. The mixture was allowed to cool to room temperature and was diluted with water. The aqueous layer was extracted with ethyl acetate (100 mL×3). The combined organic layers were washed with brine, separated and dried with MgSO4. The mixture was purified by chromatography to give (R)-2-amino-4-methyl-8-(tetrahydrofuran-3-yl)pyrido[2,3-d]pyrimidin-7(8H)-one (1.59 g, 48% yield); MS (EI) for C₁₂H₁₄N₄O₂: 247.1 (MH⁺).

Scheme L

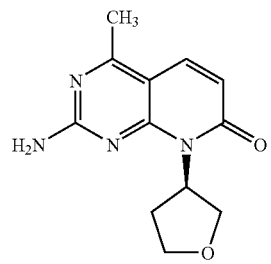

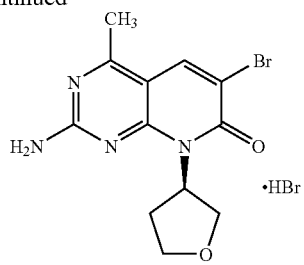

To a solution of (R)-2-amino-4-methyl-8-(tetrahydrofuran-3-yl)pyrido[2,3-d]pyrimidin-7(8H)-one (1.59 g, 6.45 mmol) in dichloromethane (50 mL) was added bromine (0.4 mL, 7.74 mmol) at room temperature. This reaction was stirred for 2 h at room temperature and monitored by LC/MS. The solvent was removed in vacuo, and then ethyl acetate was added to the resulting crude material to precipitate (R)-2-amino-6-bromo-4-methyl-8-(tetrahydrofuran-3-yl)pyrido[2,3-d]pyrimidin-7(8H)-one hydrobromide as a yellow precipitate (2.60 g, quantitative). This hydrogen bromide salt was used in the next reaction without further purification; MS (EI) for $C_{12}H_{13}BrN_4O_2$: 325.0 (M+), 327.0 (M+2).

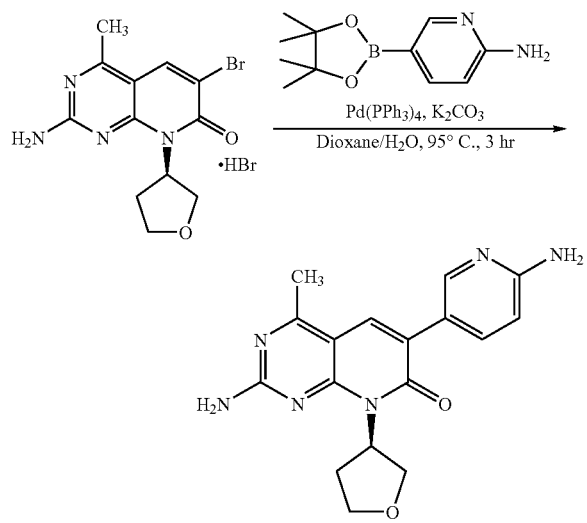

To a solution of (R)-2-amino-6-bromo-4-methyl-8-(tetrahydrofuran-3-yl)pyrido[2,3-d]pyrimidin-7(8H)-one hydrobromide (2.97 g, 7.36 mmol) in 1,4-dioxane (100 mL) and water (25 mL) were added 2-aminopyridine-5-boronic acid pinacol ester (2.43 g, 11.0 mmol), $K_2CO_3$ (3.05 g, 22.1 mmol) and $Pd(PPh_3)_4$ (170 mg, 2 mol %) under a nitrogen atmosphere. The reaction mixture was heated at 95° C. for 3 h. After the reaction was complete by LC/MS, the reaction mixture was partitioned with ethyl acetate (200 mL). The precipitate in the aqueous layer was collected by filtration. Meanwhile, the aqueous layer was washed with ethyl acetate (100 mL×3) and the organic layers with brine. The organic layers were collected and dried with $MgSO_4$, and the mixture filtered. The solvent was removed in vacuo to give a yellow solid. The combined solids were washed with ethyl acetate and water to give the desired product (1.96 g, 79% yield, >98% HPLC purity).

To the solid product was added in 1,4-dioxane (150 mL) and deionized water (50 mL) and heated to 80° C. To the homogeneous hot solution was added 98 mg of Si-SPM3 scavenging resin (5% w/w, PhosphonicS Ltd, Oxford, UK) and heated to 80° C. for 2 h. The reaction mixture was filtered on Celite while hot and rinsed with 1,4-dioxane. The filtrate was concentrated under reduced pressure until ca. 70% of the solvent had been removed. The suspension was cooled to room temperature, over about 2 h, and the solid which was precipitated was collected by filtration, washed with ethyl acetate, and dried in a high vacuum overnight to afford 2-amino-6-(6-aminopyridin-3-yl)-4-methyl-8-[(3R)-tetrahydrofuran-3-yl]pyrido[2,3-d]pyrimidin-7(8H)-one (927 mg, 37% yield, >99% purity). The filtrate was concentrated and recrystallized to give additional compound (355 mg, 14% yield, >96% purity). MS (EI) for $C_{17}H_{18}N_6O_2$: 339.2 (MH+); HPLC (>97% purity); $^1$H NMR (400 MHz, DMSO-$d_6$); δ 8.20 (s, 1H), 7.85 (s, 1H), 7.69 (dd, 1H), 7.12 (s, 2H), 6.45 (d, 1H), 6.20 (m, 1H), 6.03 (s, 2H), 4.22 (qr, 1H), 3.87 (m, 3H), 2.53 (s, 3H), 2.37 (m, 1H), 2.03 (m, 1H).

Examples 3-5 are prepared using procedures similar to those described herein.

| | $^1$HNMR (400 MHz, DMSO-$d_6$) | MS (EI) |
|---|---|---|
| Cmpd 1 | δ 8.20 (s, 1 H), 7.84 (s, 1 H), 7.70 (dd, 1 H), 7.15 (s, 2 H), 6.46 (d, 1 H), 6.04 (s, 2 H), 5.06 (bs, 1 H), 4.47 (bs, 1 H), 4.11 (m, 1 H), 3.84 (m, 1 H), 3.64 (m, 1 H), 2.85 (m, 1 H), 2.54 (s, 3 H), 1.69 (m, 3 H) | $C_{18}H_{20}N_6O_2$: 353.2 [MH]+ |

| | ¹HNMR (400 MHz, DMSO-d₆) | MS (EI) |
|---|---|---|
| 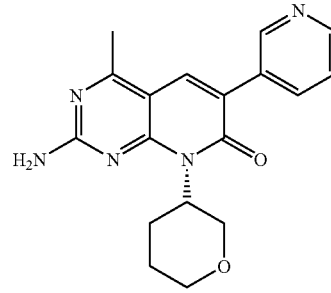<br>Cmpd 2 | δ 8.40 (s, 2 H), 8.30 (m, 3 H), 8.20 (s, 2 H), 7.55 (d, 1 H), 5.50 (brs, 1 H), 4.48 (brs, 1 H), 3.83 (m, 1 H), 3.65 (m, 1 H), 3.43 (m, 1 H), 2.81 (m, 1 H), 2.70 (s, 3 H), 1.71 (m, 3 H) | $C_{18}H_{20}N_6O_2$: 353.1 $[MH]^+$ |
| 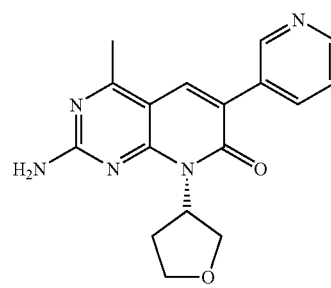<br>Cmpd 4 | δ 8.20 (s, 1 H), 7.85 (s, 1 H), 7.68 (dd, 1 H), 7.12 (s, 2 H), 6.43 (d, 1 H), 6.20 (m, 2 H), 6.03 (s, 1 H), 4.22 (q, 1 H), 3.87 (m, 3 H), 2.51 (s, 3 H), 2.36 (m, 1 H), 2.03 (m, 1 H) | $C_{17}H_{18}N_6O_2$: 339.2 $[MH]^+$ |

Utility

Suitable in vitro assays for measuring PI3K and mTOR activity and the inhibition thereof by compounds are known in the art. Compounds of this invention have been tested using the assays described in Biological Example 1 and 2 and have been determined to be inhibitors of PI3K and mTOR. Assays for measurement of in vitro efficacy in treatment of cancer are known in the art. In addition, cell-based tumor models are described in Biological Examples, Example 3 infra. An assay for measuring proliferation is described in Biological Example 4, infra. An assay for measuring mouse microsomal oxidation of compounds of the Invention is described in Biological Example 5, infra. Suitable in vivo models for cancer are known to those of ordinary skill in the art. For further details of in vivo models for breast, colon, and prostate adenocarcinoma, see Biological Examples 6, 7, and 8, infra. Following the examples disclosed herein, as well as that disclosed in the art, a person of ordinary skill in the art can determine the inhibitory activity of a compound of this invention.

As inhibitors of PI3K and mTOR, compounds of the invention are useful for treating diseases, particularly cancer in which PI3K and/or mTOR activity contributes to the pathology and/or symptomatology of the disease. For example, cancer in which PI3K and/or mTOR activity contributes to its pathology and/or symptomatology include breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), multiple myeloma, or thyroid carcinoma.

BIOLOGICAL EXAMPLES

Biological Example 1

PI3K Luciferase-Coupled Chemiluminescence Assay Protocol

PI3Kα activity is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP, substrate (PIP2), and kinase in a 20 μL volume in a buffer solution. The standard PI3Kalpha assay buffer is composed 50 mM Tris, pH 7.5, 1 mM EGTA, 10 mM $MgCl_2$, 1 mM DTT and 0.03% CHAPS. The standard assay concentrations for enzyme, ATP, and substrate are 1.5 nM, 1 μM, and 10 μM, respectively. The reaction mixture was incubated at ambient temperature for approximately 2 h. Following the kinase reaction, a 10 μL aliquot of luciferase-luciferin mix (Promega Kinase-Glo) was added and the chemiluminescence signal measured using a Victor2 plate reader (Perkin Elmer). Total ATP consumption was limited to 40-60% and IC50 values of control compounds correlate well with literature references. PI3Kα can be replaced with PI3Kβ, PI3Kδ, or PI3Kγ to determine the compound's activity for the other isoforms of PI3K.

Biological Example 2 mTOR/GbL/Raptor (mTORC1) ELISA Assay

The measurement of mTORC1 enzyme activity was performed in an ELISA assay format following the phosphorylation of 4E-BP1 protein. All experiments were performed in the 384-well format. Generally, 0.5 μL DMSO containing varying concentrations of the test compound was mixed with 15 µL enzyme solution. Kinase reactions were initiated with the addition of 15 µL of substrates-containing solution. The assay conditions were as follows; 0.2 nM mTORC1, 10 µM ATP and 50 nM NHis-tagged 4E-BP1 in 20 mM Hepes, pH 7.2, 1 mM DTT, 50 mM NaCl, 10 mM $MnCl_2$, 0.02 mg/mL BSA, 0.01% CHAPS, 50 mM (3-glycerophosphate. Following an incubation of 120 minutes at ambient temperature, 20 µL of the reaction volume was transferred to a Ni-Chelate-coated 384-well plate. The binding step of the 4E-BP1 protein proceeded for 60 minutes, followed by washing 4 times each with 50 µL of Tris-buffered saline solution (TBS). Anti-phospho-4E-BP1 rabbit-IgG (20 µL, 1:5000) in 5% BSA-TBST (0.2% Tween-20 in TBS) was added and further incubated for 60 minutes. Incubation with a secondary HRP-tagged anti-IgG was similarly performed after washing off the primary antibody (4 washes of 50 µL). Following the final wash step with TBST, 20 µL of SuperSignal ELISA Femto (Pierce Biotechnology) was added and the luminescence measured using an EnVision plate reader.

Biological Example 3 pS6 (S240/244) ELISA Assay

PC-3 and MCF-7 cells (both from ATCC) were seeded at 8×10³ cells per well in 96-well plates (Corning, 3904) in DMEM (Cellgro) containing 10% FBS (Cellgro), 1% NEAA (Cellgro) and 1% penicillin-streptomycin (Cellgro). Two plates were prepared for cell fixation ELISA, one for pS6 (S240/244) and one for total S6. Cells were incubated at 37° C., 5% CO2 for 48 h, and the growth medium was replaced with serum-free DMEM. Serial dilutions of the test compound in 0.3% DMSO (vehicle) were added to the cells and incubated for 3 h. To fix the cells, medium was removed and 100 µL/well of 4% formaldehyde (Sigma Aldrich, F8775) in TBS (20 mM Tris, 500 mM NaCl) was added to each well at RT for 30 min. Cells were washed 3 times with 200 µL TBS containing 0.1% Tween20 (Bio-Rad, catalog #170-6351) (TBST), and quenched with 100 µL 0.6% H2O2 (VWR International, catalog #VW3742-1) in TBST for 30 min at RT. Plates were washed 3 times with 200 µL TBST and blocked with 100 µL 5% BSA (Jackson ImmunoResearch, 001-000-173) in TBST for 1 h at RT. Anti-pS6 (S240/244) antibody (Cell Signaling Technology, 2215) and anti-total-S6 antibody (Cell Signaling Technology, 2217) were diluted 1/500 in 5% BSA in TBST, and 50 µL of either primary antibody solution was added to one plate to detect pS6 or total S6. After incubation overnight at 4° C., plates were washed 4 times with 200 µL TBST. Goat anti-rabbit secondary antibody (Jackson ImmunoResearch, catalog #111-035-003) was diluted at 1/15000 in 5% BSA in TBST. 100 µL of antibody solution was added to each well and incubated for 1 h at RT. Plates were washed 3 times with 200 µL TBST and 2 times with 200 µL TBS. Chemiluminescent substrate (Super Signal Elisa Femto Chemiluminescent Substrate; Pierce, 37075) was prepared at RT. One-hundred µL of chemiluminescent substrate per well was added and then the plate was shaken for 1 min. Luminescence was read immediately on a Wallac plate reader. IC50 values were determined based on the ratio of pS6 to total S6 signal for compound treated wells, normalized to the DMSO-treated control wells.

Biological Example 4

MCF-7 and PC-3 2 Day BrdU Cell Proliferation Assay

MCF-7 (ATCC) and PC-3 (ATCC) cells were seeded onto 96-well plates (Corning, #3904) in their growth medium, DMEM (Cellgro, #10-014-CV)+10% heat-inactivated FBS (Invitrogen)+1% Pen/Strep (Cellgro, #30-002-CI)+1% NEAA (Cellgro, #25-025-CI) at a seeding density of 15000 and 8000 cells/well, respectively. Cells were incubated overnight at 37° C., 5% $CO_2$. Cells were then treated the next day with a serial dilution of compound in its growth medium (containing a final concentration of 0.3% DMSO). Triplicate wells were used for each compound concentration. The control wells received 0.3% DMSO in growth medium. The plates were incubated at 37° C., 5% $CO_2$ for an additional 48 hr. Cells were labeled with BrdU (Roche, #10280879001, 20 µM) for 2-4 hr and then fixed with 70% EtOH+0.1 M NaOH for 30 min at RT. Anti-BrdU-Peroxidase (Roche, #11585860001, 1/2000 in PBS+1% BSA) conjugate was added to the cells, after which the plates were washed 3 times with 1×PBS. Chemiluminescent substrate solution (Pierce, #3707A/B) was added, and the plates were read for luminescence using the Wallac Victor plate reader for 0.1 sec. $IC_{50}$ values were determined based on cell proliferation with compound treatment compared to the 0.3% DMSO vehicle control.

Biological Example 5

Mouse Microsomal Oxidation Assay

Microsomal oxidation of test compounds in the presence of mouse liver microsomal fractions was conducted in 96-well microtiter plates. Liver microsomal preparations were purchased from BD Gentest (Cat #452701). Test compounds were incubated in duplicate at 37° C. for 30 min in the presence of liver microsomes and NADPH. Reaction mixtures (75 µL) contained a final concentration of 15 µM test compound, 0.15% DMSO, 0.5 mg/mL microsomal protein and 1 mM NADPH in 100 mM potassium phosphate, pH 7.4 buffer. Control incubations contained the full complement of enzyme and substrate but no NADPH added. All test-sets included reference CYP450 substrates to verify assay performance. Reactions were terminated by the addition of 150 µL acetonitrile containing 0.1% formic acid. The concentration of the test compound remaining was determined by LC/MS/MS analysis on Sciex API-3000 instrument. The % oxidation is determined by the change in peak integration for the test compound (+/−NADPH) relative to the peak integration of internal standard injected with the sample:

% oxidation=[((Int. peak$_{compound, no NADPH}$/Int. peak$_{standard}$)−(Int. peak$_{compound, NADPH}$/ Int. peak$_{standard}$))/100]

Chromatographic separation of analytes was achieved using a Phenomenex Synergi Hydro-RP column (Torrance, Calif.) and a mobile phase consisting of 0.1% formic acid in acetonitrile and 0.1% formic acid in water. A linear gradient from 2-98% acetonitrile was used to elute compounds from the HPLC column. The typical variation (ie, precision) observed in the measurements for a given sample (e.g., multiple injections of the same sample) is ca. 10%, and thus experimental values of +/−10% can be considered to be equivalent to little or no oxidation. Large negative experimental values (negative values >10%) could suggest the potential NADPH-independent metabolism of the compounds.

Biological Example 6-8

Pharmacodynamic Xenograft Tumor Models

Female and male athymic nude mice (NCr) 5-8 weeks of age and weighing approximately 20-25 g were used in the following models. Prior to initiation of a study, the animals were allowed to acclimate for a minimum of 48 h. During these studies, animals were provided food and water ad libitum and housed in a room conditioned at 70-75° F. and 60% relative humidity. A 12 h light and 12 h dark cycle was maintained with automatic timers. All animals were examined daily for compound-induced or tumor-related deaths.

MCF-7 Breast Adenocarcinoma Model

MCF7 human mammary adenocarcinoma cells were cultured in vitro in DMEM (Cellgro) supplemented with 10% Fetal Bovine Serum (Cellgro), Penicillin-Streptomycin and non-essential amino acids at 37° C. in a humidified 5% $CO_2$ atmosphere. On day 0, cells were harvested by trypsinization, and $5 \times 10^6$ cells in 100 µL of a solution made of 50% cold Hanks balanced salt solution with 50% growth factor reduced matrigel (Becton Dickinson) implanted subcutaneously into the hind flank of female nude mice. A transponder was implanted into each mouse for identification and data tracking, and animals were monitored daily for clinical symptoms and survival.

Tumors were established in female athymic nude mice and staged when the average tumor weight reached 100-200 mg. A Compound of the Invention was orally administered as a solution/fine suspension in water (with 1:1 molar ratio of 1 N HCL) once-daily (qd) or twice-daily (bid) at 10, 25, 50 and 100 mg/kg for 14 days. During the dosing period of 14-19 days, tumor weights were determined twice-weekly and body weights were recorded daily.

Colo-205 Colon Model

Colo-205 human colorectal carcinoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization, and $3 \times 10^6$ cells (passage 10-15, >95% viability) in 0.1 mL ice-cold Hank's balanced salt solution were implanted intradermally in the hind-flank of 5-8 week old female athymic nude mice. A transponder was implanted in each mouse for identification, and animals were monitored daily for clinical symptoms and survival.

Tumors were established in female athymic nude mice and staged when the average tumor weight reached 100-200 mg. A Compound of the Invention was orally administered as a solution/fine suspension in water (with 1:1 molar ratio of 1 N HCL) once-daily (qd) or twice-daily (bid) at 10, 25, 50 and 100 mg/kg for 14 days. During the dosing period of 14 days, tumor weights were determined twice-weekly and body weights were recorded daily.

PC-3 Prostate Adenocarcinoma Model

PC-3 human prostate adenocarcinoma cells were cultured in vitro in DMEM (Mediatech) supplemented with 20% Fetal Bovine Serum (Hyclone), Penicillin-Streptomycin and non-essential amino acids at 37° C. in a humidified 5% $CO_2$ atmosphere. On day 0, cells were harvested by trypsinization and $3 \times 10^6$ cells (passage 10-14, >95% viability) in 0.1 mL of ice-cold Hank's balanced salt solution were implanted subcutaneously into the hind flank of 5-8 week old male nude mice. A transponder was implanted in each mouse for identification, and animals were monitored daily for clinical symptoms and survival.

Tumors were established in male athymic nude mice and staged when the average tumor weight reached 100-200 mg. A Compound of the Invention was orally administered as a solution/fine suspension in water (with 1:1 molar ratio of 1 N HCl) once-daily (qd) or twice-daily (bid) at 10, 25, 50, or 100-mg/kg for 19 days. During the dosing period of 14-19 days, tumor weights were determined twice-weekly and body weights were recorded daily.

For subcutaneous or intradermal tumors, the mean tumor weight of each animal in the respective control and treatment groups was determined twice weekly during the study. Tumor weight (TW) was determined by measuring perpendicular diameters with a caliper, using the following formula:

$$\text{tumor weight (mg)} = [\text{tumor volume} = \text{length (mm)} \times \text{width}^2 \text{(mm}^2)]/2$$

These data were recorded and plotted on a tumor weight vs. days post-implantation line graph and presented graphically as an indication of tumor growth rates. Percent inhibition of tumor growth (TGI) is determined with the following formula:

$$\left(1 - \left(\frac{(X_f - X_0)}{(Y_f - X_0)}\right)\right) * 100$$

where
$X_0$=average TW of all tumors on group day
$X_f$=TW of treated group on Day f
$Y_f$=TW of vehicle control group on Day f If tumors regress below their starting sizes, then the percent tumor regression is determined with the following formula:

$$\left(\frac{(X_0 - X_f)}{X_0}\right) * 100$$

Tumor size is calculated individually for each tumor to obtain a mean±SEM value for each experimental group. Statistical significance is determined using the 2-tailed Student's t-test (significance defined as P<0.05).

The foregoing invention has been described in some detail by way of illustration and example, for purposes of clarity and understanding. The invention has been described with reference to various specific embodiments and techniques. However, it should be understood that many variations and modifications may be made while remaining within the spirit and scope of the invention. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:
1. A Compound of Formula I:

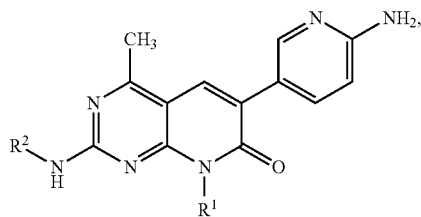

optionally as single stereoisomer or mixture of stereoisomers thereof, and additionally optionally as a pharmaceutically acceptable salt thereof, wherein
$R^1$ is tetrahydrofuranyl or tetrahydropyranyl; and
$R^2$ is hydrogen or alkyl.

2. The Compound of claim 1, or a single stereoisomer or mixture of stereoisomers thereof, where $R^2$ is hydrogen; optionally as a pharmaceutically acceptable salt thereof.

3. The Compound of claim 1, or a single stereoisomer or mixture of stereoisomers thereof, where $R^2$ is alkyl; optionally as a pharmaceutically acceptable salt thereof.

4. The Compound of claim 1 or a single stereoisomer or mixture of stereoisomers thereof, where $R^1$ is tetrahydrofuranyl; optionally as a pharmaceutically acceptable salt thereof.

5. The Compound of claim 1 or a single stereoisomer or mixture of stereoisomers thereof, where $R^1$ is tetrahydropyranyl; optionally as a pharmaceutically acceptable salt thereof.

6. The Compound of claim 1 where the Compound of Formula I is according to Formula Ia

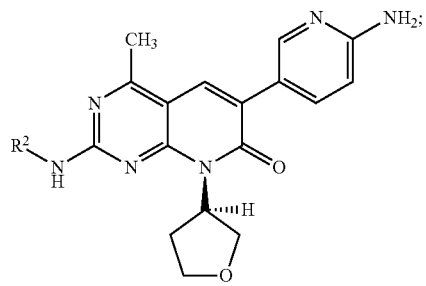

optionally as a pharmaceutically acceptable salt thereof.

7. The Compound of claim 1 where the Compound of Formula I is according to Formula Ib

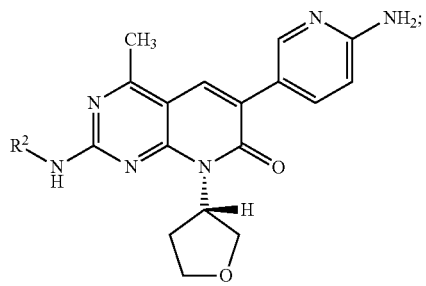

optionally as a pharmaceutically acceptable salt thereof.

8. The Compound of claim 1 where the Compound of Formula I is according to Formula Ic

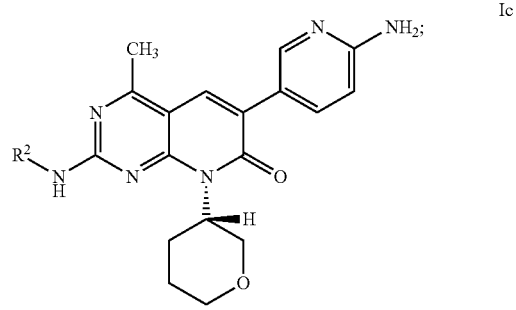

optionally as a pharmaceutically acceptable salt thereof.

9. The Compound of claim 1 where the Compound of Formula I is according to Formula Id

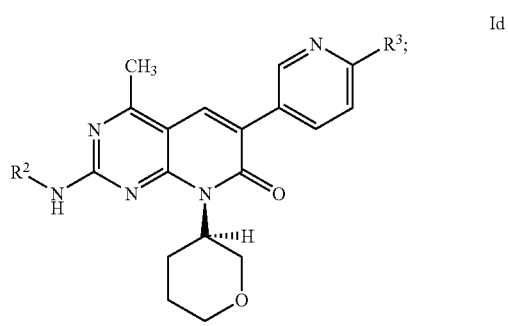

optionally as a pharmaceutically acceptable salt thereof.

10. The Compound of claim 1 where the Compound of Formula I is according to Formula Ie

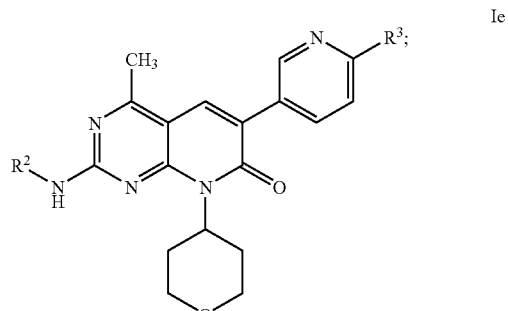

optionally as a pharmaceutically acceptable salt thereof.

11. The Compound of claim 1 selected from 2-amino-6-(6-aminopyridin-3-yl)-4-methyl-8-(tetrahydro-2H-pyran-3-yl)pyrido[2,3-d]pyrimidin-7(8H)-one;
2-amino-6-(6-aminopyridin-3-yl)-4-methyl-8-[(3S)-tetrahydro-2H-pyran-3-yl]pyrido[2,3-d]pyrimidin-7(8H)-one;
2-amino-6-(6-aminopyridin-3-yl)-4-methyl-8-(tetrahydro-2H-pyran-4-yl)pyrido[2,3-d]pyrimidin-7(8H)-one;
2-amino-6-(6-aminopyridin-3-yl)-4-methyl-8-[(3S)-tetrahydrofuran- -continued 3-yl]pyrido[2,3-d]pyrimidin-7(8H)-one; and
2-amino-6-(6-aminopyridin-3-yl)-4-methyl-8-[(3R)-tetrahydrofuran-3-yl]pyrido[2,3-d]pyrimidin-7(8H)-one;
optionally as a pharmaceutically acceptable salt thereof.

12. The Compound of claim 10 named 2-amino-6-(6-aminopyridin-3-yl)-4-methyl-8-(tetrahydro-2H-pyran-4-yl)pyrido[2,3-c]pyrimidin-7(8H)-one optionally as a pharmaceutically acceptable salt thereof.

13. The Compound of claim 6 named 2-amino-6-(6-aminopyridin-3-yl)-4-methyl-8-[(3R)-tetrahydrofuran-3-yl]pyrido[2,3-d]pyrimidin-7(8H)-one optionally as a pharmaceutically acceptable salt thereof.

14. A pharmaceutical composition which comprises a compound of claim 1 optionally as a single stereoisomer or mixture of stereoisomers thereof and additionally optionally as a pharmaceutically acceptable salt thereof, and a pharmaceutically acceptable carrier, excipient, or diluent.

15. A pharmaceutical composition which comprises the compound of claim 12, optionally as a pharmaceutically acceptable salt thereof, and a pharmaceutically acceptable carrier, excipient, or diluent.

16. A pharmaceutical composition which comprises the compound of claim 13, optionally as a pharmaceutically acceptable salt thereof, and a pharmaceutically acceptable carrier, excipient, or diluent.

* * * * *